(12) United States Patent
Malarkannan

(10) Patent No.: US 10,786,532 B2
(45) Date of Patent: Sep. 29, 2020

(54) METHOD OF PROVIDING CELLULAR THERAPY USING MODIFIED NATURAL KILLER CELLS OR T LYMPHOCYTES

(71) Applicant: Versiti Blood Research Institute Foundation, Inc., Milwaukee, WI (US)

(72) Inventor: Subramaniam Malarkannan, Menomonee Falls, WI (US)

(73) Assignee: VERSITI BLOOD RESEARCH INSTITUTE FOUNDATION, INC., Milwaukee, WI (US)

( * ) Notice: Subject to any disclaimer, the term of this patent is extended or adjusted under 35 U.S.C. 154(b) by 0 days.

(21) Appl. No.: 14/433,082

(22) PCT Filed: Sep. 30, 2013

(86) PCT No.: PCT/US2013/062632
§ 371 (c)(1),
(2) Date: Apr. 2, 2015

(87) PCT Pub. No.: WO2014/055413
PCT Pub. Date: Apr. 10, 2014

(65) Prior Publication Data
US 2015/0258143 A1   Sep. 17, 2015

Related U.S. Application Data

(60) Provisional application No. 61/866,348, filed on Aug. 15, 2013, provisional application No. 61/708,837, filed on Oct. 2, 2012.

(51) Int. Cl.
| | |
|---|---|
| *A61K 35/17* | (2015.01) |
| *A61K 38/17* | (2006.01) |
| *A61K 35/545* | (2015.01) |
| *G01N 33/50* | (2006.01) |

(52) U.S. Cl.
CPC ............ *A61K 35/17* (2013.01); *A61K 35/545* (2013.01); *G01N 33/502* (2013.01); *A61K 38/17* (2013.01); *G01N 2500/10* (2013.01)

(58) Field of Classification Search
None
See application file for complete search history.

(56) References Cited

U.S. PATENT DOCUMENTS 7,446,190 B2 * 11/2008 Sadelain ................ C07H 21/04
536/23.4
2002/0037286 A1   3/2002 Krause et al.
2003/0059924 A1   3/2003 Mancebo et al.
2004/0214783 A1  10/2004 Terman
2010/0135974 A1   6/2010 Eshhar et al.

FOREIGN PATENT DOCUMENTS

| WO | 200127294 A1 | 4/2001 |
| WO | 200250263 a2 | 6/2002 |
| WO | 2005001114 A2 | 1/2005 |

OTHER PUBLICATIONS

Morgan et al., Molecular Therapy, 2010, 18: 843-851.*
Hara et al., J. Immunol., 2008, 181: 918-930.*
Ye et al., Nature, 2002, 418: 443-447.*
Zahn et al., Gene Therapy, 2008, 15: 1210-1222.*
Cooper et al., Blood., 2003, 101: 1637-1644.*
Kalos et al., Sci Transl. Med., Aug. 10, 2011, 3: 1-11.*
Tian et al., Transplantation, 2007, 84: 400-406.*
Toshchakov et al., Expert OPin. Biol. Ther., 20078, 7: 1035-1050.*
Raab et al., J. Biol. Chem., 1999, 274: 21170-21179.*
Geng et al., J. Immunol., 1999, 163: 5753-5757.*
Kochenderfer et al., Blood, online Dec. 8, 2011, 119: 2709-2720.*
Griffith et al., Science, 2001, 293: 2261-2263.*
Morgan et al., (Mol. Ther., 2010, 18: 843-851.*
Kwon et al., EMBO J., 2005, 24: 2331-2341.*
International Search Report and Written Opinioin under dated Apr. 18, 2014 in connection with PCT/US2013/62632.
Rajasekaran K, et al. "Fyn-ADAP signaling via Carma1-Bcl10-MAP3K7 signalosome exclusively regulates inflammatory cytokine production in NK cells." Nat Immunol., 2013, 14(11):doi:10.1038/ni.2708.
Rajasekaran K, et al. "TAK1 regulates NK cell-mediated cytotoxicity and cytokine production." J. Biol. Chem. 2011.

* cited by examiner

*Primary Examiner* — Ileana Popa
(74) *Attorney, Agent, or Firm* — Quarles & Brady LLP

(57) ABSTRACT

A method of decreasing cytokine production and release is disclosed. In one embodiment, the method comprises the step of providing cytotoxic cells to a subject wherein the cells are preferably natural killer cells or T lymphocytes and are genetically modified to express a chimeric antigen receptor comprising a first element that is an extracellular antigen receptor and a second intracellular element that is a signaling moiety comprising altered ADAP-dependent or Fyn-dependent signaling such that downstream signaling causing cytokine release is decreased. Specific modifications of CD137 and NKG2D cytoplasmic tails are described. Additionally, methods to develop and screen drug compounds capable of compromising the binding between ADAP and Fyn and disrupting the downstream release of cytokines are described.

37 Claims, 16 Drawing Sheets

Specification includes a Sequence Listing.

METHOD OF PROVIDING CELLULAR THERAPY USING MODIFIED NATURAL KILLER CELLS OR T LYMPHOCYTES

CROSS-REFERENCE TO RELATED APPLICATIONS

This application represents the national stage entry of PCT International Application No. PCT/US2013/062632 filed Sep. 30, 2013, which claims the benefit of U.S. Provisional Patent Application No. 61/866,348, filed on Aug. 15, 2013, and U.S. Provisional Patent Application No. 61/708,837, filed Oct. 2, 2012. The disclosures of which are incorporated herein by reference for all purposes.

STATEMENT REGARDING FEDERALLY SPONSORED RESEARCH OR DEVELOPMENT

This invention was made with government support under Grant Nos. 5R01 AI 064828 and 1R01 AI 102893, awarded by the National Institute of Allergy and Infectious Diseases of the National Institutes of Health. The U.S. Government has certain rights in this invention.

BACKGROUND OF THE INVENTION

CD137 belongs to the tumor necrosis factor receptor superfamily and functions as a co-stimulatory receptor in T cells. CD137 interacts with CD137L (4-1BBL), which is expressed on dendritic cells, macrophages, epithelial cells, B cell lymphomas, and other tumor cells. Cross-linking of CD137 by an agonistic antibody transmits a potent co-stimulatory signal in $CD4^+$ and $CD8^+$ T cells. This discovery has led to the use of the CD137 cytoplasmic domain as a signal transducer for chimeric antigen receptors (CARs). CARs are fusion proteins that include the variable regions of tumor antigen-specific antibodies, such as anti-CD19, and cytoplasmic domains from CD3ζ, CD28 and CD137. T cells genetically modified to express these CARs efficiently kill tumor cells. See Jang et al, *Biochem. Biophys. Res. Commun.* 242:613-620 (1998). However, CAR-transduced T cells can also cause significant toxicities, including cytokine release syndrome in some patients. Therefore, there remains a need in the art for methods of identifying unique signaling molecules that are exclusively responsible for NK or T cell-mediated cytotoxicity but not inflammatory cytokine production, and for improved immunotherapy protocols.

SUMMARY OF THE INVENTION

In a first aspect, the present invention is summarized as a method of decreasing or preventing cytokine production in a subject. The method includes the step of providing to a subject a cytotoxic cell genetically modified to express a chimeric antigen receptor comprising a first element and a second element. The first element is a receptor and the second element is a signaling moiety comprising one or more modifications that disrupt cytokine release while maintaining cytotoxic potential of the genetically modified cell in the subject relative to a cytotoxic cell not expressing the chimeric antigen receptor. The cytotoxic cell can be a Natural Killer (NK) cell or a T lymphocyte. Cytotoxicity of the cytotoxic cell can be substantially unchanged relative to a cytotoxic cell not expressing the chimeric antigen receptor. The cytotoxic cell can be autologous to the subject. The cytotoxic cell can be derived from bone marrow of the subject, The cytotoxic cell can be derived from a stem cell. The stem cell can be a human pluripotent stem cell such as an induced pluripotent stem cell obtained from a somatic cell of the subject.

In some cases, the chimeric antigen receptor can have specificity for a subset of immune cells. The chimeric antigen receptor can have specificity for a tumor antigen, a bacterial antigen, or a viral antigen. The extracellular element of the chimeric antigen receptor can be a ligand. The signaling moiety can comprise a CD137 cytoplasmic tail. The genetically modified cytotoxic cell can express a decoy polypeptide. The decoy polypeptide can be covalently linked to the CAR, expressed as a separate polypeptide from the CAR, or expressed using a vector comprising an IRES sequence.

In a preferred embodiment, the signaling moiety of the CAR comprises at least a portion of an ADAP or Fyn polypeptide, which is expressed after an internal ribosomal entry site (IRES) sequence so that the ADAP or Fyn polypeptide can be expressed in the cell cytosol and function as a decoy polypeptide. The ADAP or Fyn polypeptide can be expressed independently of the IRES sequence and potentially function as a decoy polypeptide. Additionally, the ADAP or Fyn polypeptide can be expressed so that it contacts to a second element of the CAR responsible for intracellular signaling. The signaling moiety can comprise at least 3 contiguous amino acids selected from residues 600-630 of SEQ ID NO:1. The 3 contiguous amino acids can be selected from residues 619-630 of SEQ ID NO:1. In other cases, the signaling moiety comprises at least 3 contiguous amino acids selected from residues 600-640 of SEQ ID NO:1. The signaling moiety can comprise at least 3 contiguous amino acids selected from residues 619-630 of SEQ ID NO:1. The signaling moiety can comprise at least 3 contiguous amino acids of an amino acid sequence selected from the group consisting of SEQ ID NOS:1, 2, and 3. The at least 3 amino acids can comprise at least one conservative amino acid substitution or non-conservative amino acid substitution, whereby the signaling moiety has increased stability or longer half-life relative to a signaling moiety lacking the at least one amino acid substitution.

In another aspect, the present invention can be summarized as providing a genetically modified cytotoxic cell. The genetically modified cytotoxic cell can express a chimeric antigen receptor comprising, a first element and a second element. The first element is a receptor and the second element is a signaling moiety comprising one or more modifications that disrupt cytokine release while maintaining cytotoxic potential of the genetically modified cell in the subject relative to a cytotoxic cell not expressing the chimeric antigen receptor.

In a further aspect, the present invention can be summarized as providing a method of screening for compounds that inhibit ADAP-dependent signaling. The method can include the step of assaying a library of small molecules for specific binding to at least a portion of an ADAP or Fyn polypeptide or reduced or inhibited function of ADAP or Fyn. The method can further comprise using one or more polypeptides of at least 3 contiguous amino acids from a sequence corresponding to residues 600-640 or residues 619-630 of SEQ ID NO:1 or using one or more polypeptides of at least 3 contiguous amino acids of SEQ ID NO:2.

In another aspect, the present invention can be summarized as providing a method of reducing toxic cytokine release from an immune cell. The method can include the steps of contacting an immune cell to a compound that blocks an interaction between at least a portion of a FYN polypeptide and at least a portion of an ADAP polypeptide, where cytotoxicity of the immune cell is substantially unaffected, and where toxic cytokine release from the immune cell is reduced relative to an immune cell not contacted to the compound. In some cases, the compound is a small molecule. The interaction can be blocked in vitro or in vivo.

(upper panel), EL4$^{H60-Hi}$ (middle panel) or EL4$^{4-1BBL-Hi}$ (lower panel) stable cell lines. Data is a compilation of three independent experiments (Mean+std. dev., Student's t test *P<0.05, P<0.01, *P<0.001, NS, not significant). This set of data indicates that in the absence of ADAP or Carma1 proteins the ability of NK cells to produce inflammatory cytokines significantly decreases.

Figure 1:
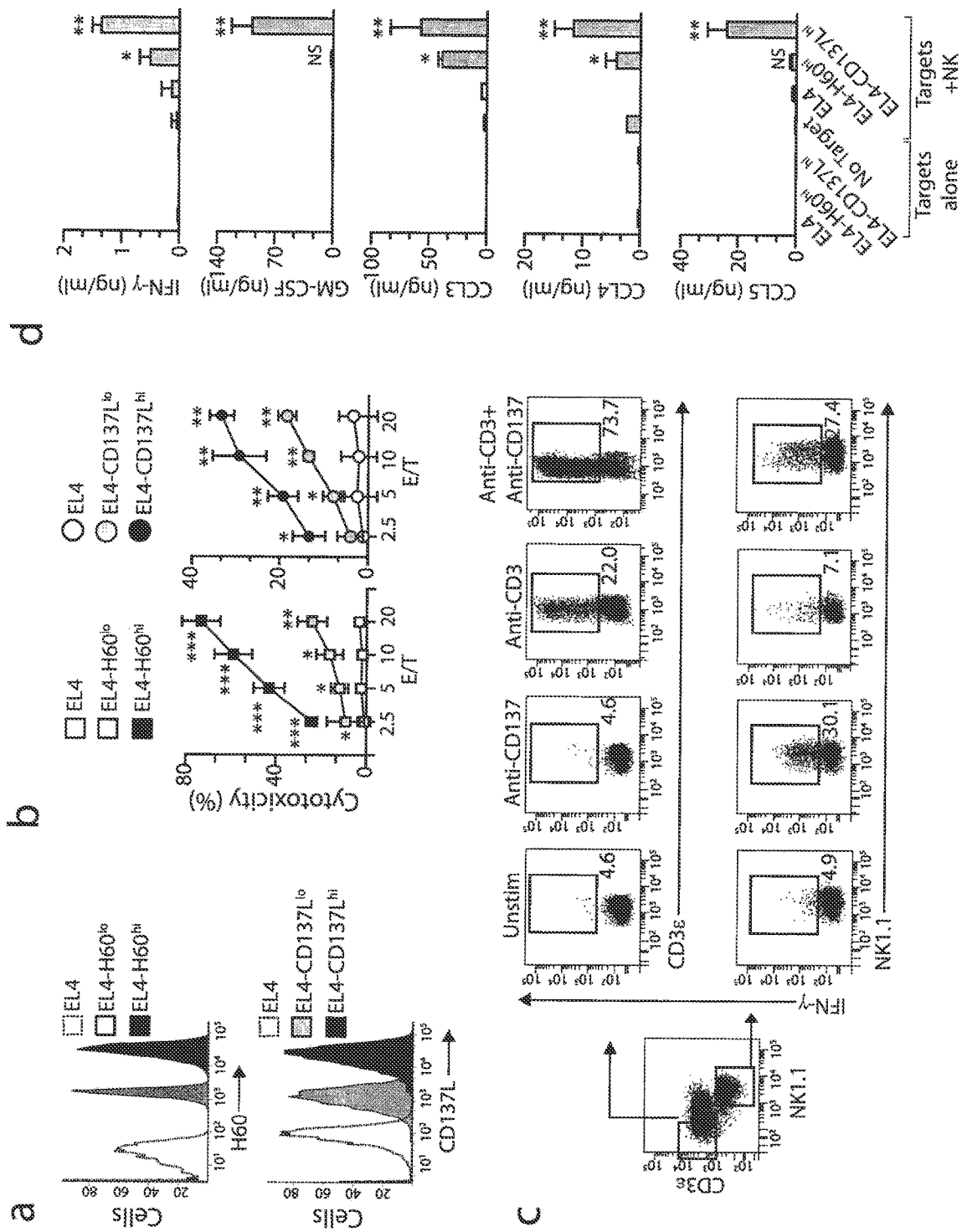
FIG. 1 presents data demonstrating that CD137 functions as an independent activation receptor in NK cells. (a) Flow cytometry analyses of CD137L (top) and H60 (bottom) expression in EL4 cells stably transfected with plasmids-encoding the corresponding genes. Histogram with dotted line indicates background levels of CD137L or H60 expression in parental EL4 cells. Histogram in grey represents the ligand expression in $EL4^{CD137L-Low}$ or $EL4^{H60-Low}$. Histogram in black represents the ligand expression in $EL4^{CD137L-High}$ or $EL4^{H60-High}$ stable cell lines. (b) Average percent cytotoxicity with standard deviation of IL-2-expanded WT NK cells following co-culture with indicated target cells. *P<0.001 versus EL4 (Student's t-test). (c) IntracellularIFN-γ staining in IL-2-cultured $CD3^+NK1.1^+$ T and $CD3^+NK1.1^+$ NK cells from WT mice either left unstimulated or stimulated with plate-bound anti-CD3, anti-CD137 mAb alone or in combination for 12 hours. (d) Quantitative analyses of IFN-γ, GM-CSF, MIP-1α, MIP-1β and RANTES from WT NK cells following 18 hour co-culture with indicated target cells using bioplex assays. (Mean+std. dev., Student's t test *P<0.05, P<0.01, *P<0.001, NS, not significant). Data in a-d are representatives of at least three independent experiments. These results show that CD137 activates NK cells to kill tumor cells and to produce inflammatory cytokines.
Figure 2:
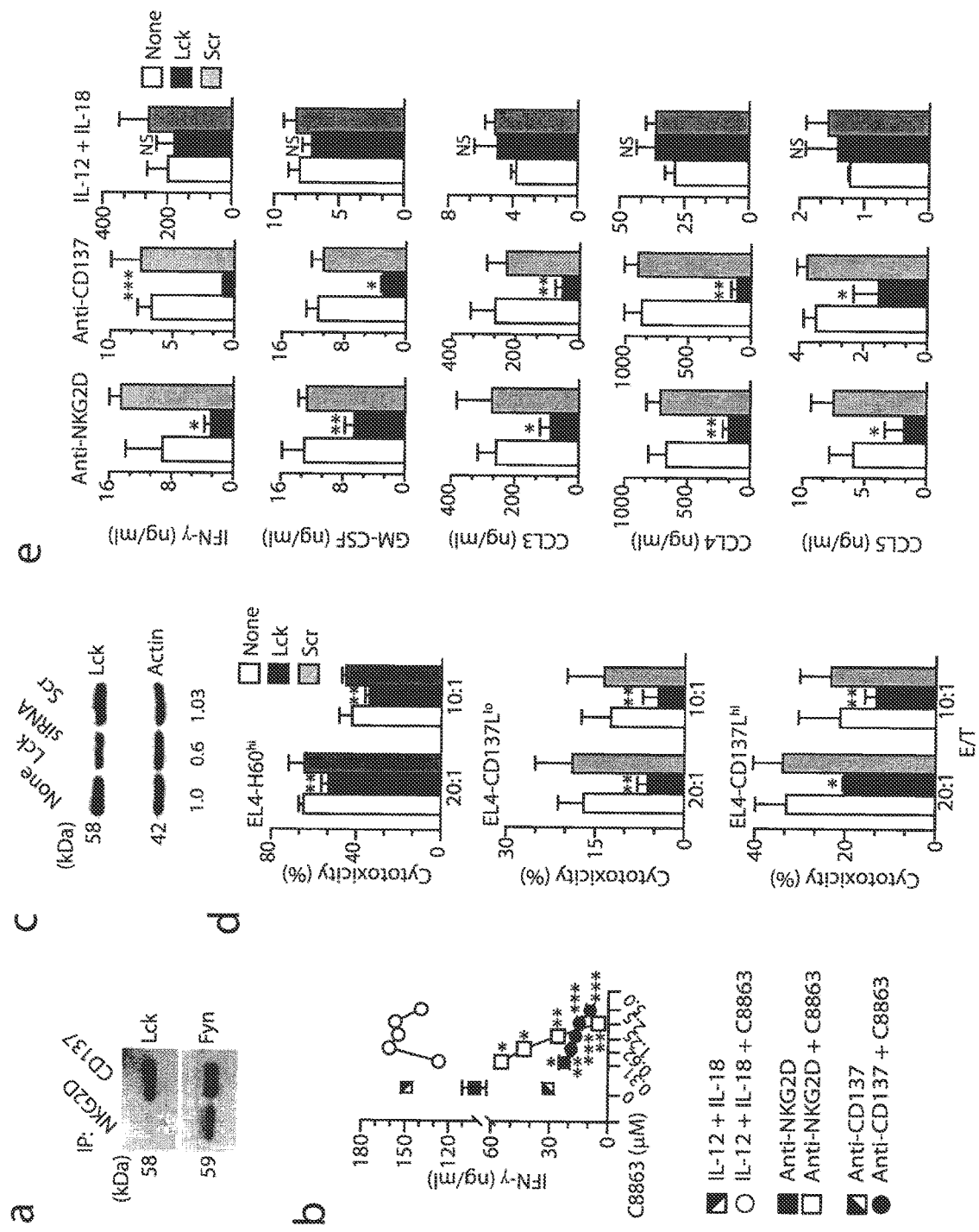
FIG. 2 presents data demonstrating that Lck is crucial in CD137-mediated signaling. (a) Immunoblot analyses of Lck and Fyn following immunoprecipitation of NKG2D and CD137 receptors in unstimulated, IL-2-expanded WT NK cells, (b) Quantitative analysis of IFN-γ production from NK cells after pre-incubation with Lck inhibitor, C8863. Open squares, inhibitor-treated NK cells with anti-NKG2D monoclonal antibody (mAb) activation; filled circles, inhibitor treated NK cells with anti-CD137 mAb activation, open circles, inhibitor-treated NK cells with IL-12 and IL-18 activation. Cytokine production in the DMSO (Vehicle)-treated NK cells in response to anti-NKG2D, anti-CD137 or IL-12 and IL-18 are indicated as closed or half-filled squares. (Mean+std. dev., Student's t test *P<0.05, P<0.01, *P<0.001, NS, not significant for inhibitor-treated versus DMSO (vehicle)-treated). (c) Western blot for Lck in NK cells following mock, Lck-specific and scrambled siRNA transfections. Actin expression was used as an internal loading control. Fold change in Lck expression was determined by densitometry following normalization with actin. (d) Bar diagram represents the average percent cytotoxicity with standard deviation of NK cells transfected with mock (open), scrambled siRNA (grey) or Lck-specific siRNA (black) against indicated target cells. (e) Quantitative analyses of cytokine and chemokine production, following activation with anti-CD137 (left) and anti-NKG2D (right) mAbs in WT NK cells transfected with mock, scrambled or Lck-specific siRNA. (d & e represent mean+std. dev., Student's t test *P<0.05, P<0.01, *P<0.001, NS, not significant versus scrambled siRNA-treated (t-test). Data in a-e are representatives of at least three independent experiments. These results demonstrate that protein tyrosine kinase, Lck plays an important role in regulating the signaling events via CD137 and thereby NK cell effector functions.
Figure 3:
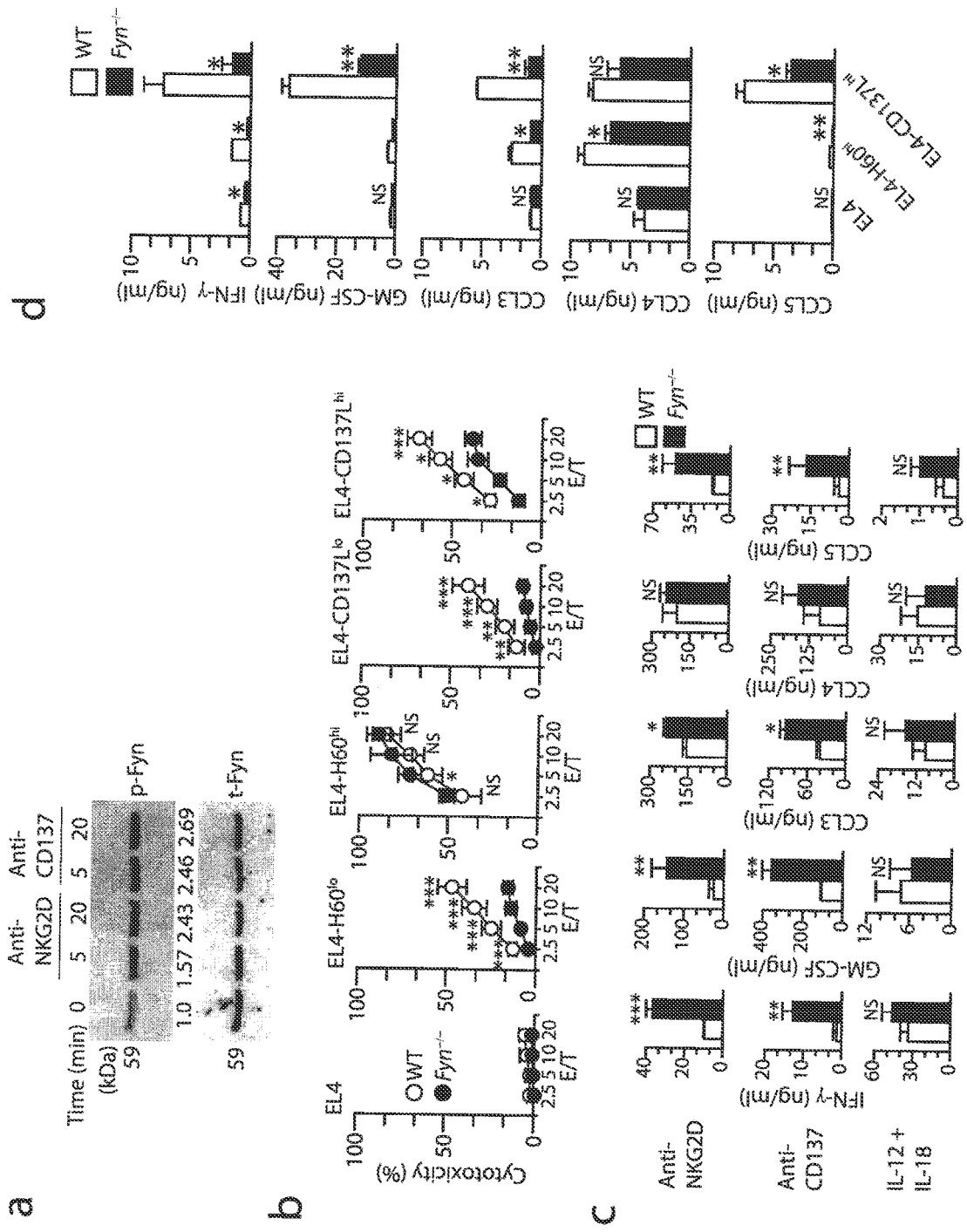
FIG. 3 presents data demonstrating that Fyn plays a critical role in mediating NK cell effector functions. (a) Immunoblot analyses of phosphorylated (pTyr530) and total Fyn in NK cells that are left unstimulated or stimulated with plate-bound anti-NKG2D or anti-CD137 mAbs. Fold change in tyrosine phosphorylation is shown at the bottom. (b) Western blot analysis of Fyn in WT and $Fyn^{-/-}$ NK cells. (c) Cytotoxic potentials of WT (open circles) and $Fyn^{-/-}$ (closed circles) NK cells to $H60^+$ and $CD137L^+$ target cells. Conventional $^{51}$Cr-release assays were performed using WT or $Fyn^{-/-}$ NK cells against indicated target cells. Average percent cytotoxicity with standard deviation is shown. (d) Quantitative analyses of IFN-γ, GM-CSF, MIP-1α, MIP-1β and RANTES from WT and $Fyn^{-/-}$ NK cells following activation with plate-bound anti-NKG2D or anti-CD137 mAbs or with a combination of IL-12 and IL-18 for 18 hours. Basal cytokine and chemokine production with no stimulation is also indicated. (e) Quantitative analyses of IFN-γ, GM-CSF, MIP-1α, MIP-1β and RANTES from WT and $Fyn^{-/-}$ NK cells following coculture with EL4, $EL4^{H60-Hi}$ or $EL4^{CD137L-Lo}$ target cells for 18 hours. Panels c-e represent mean+std. dev., Student's t test *P<0.05, P<0.01, *P<0.001, NS, not significant versus WT NK cells. Data in a-e are representatives of at least three independent experiments. This set of data proves that Fyn tyrosine kinase is important in to mediate optimal levels of tumor cytotoxicity and inflammatory cytokine production.
Figure 4:
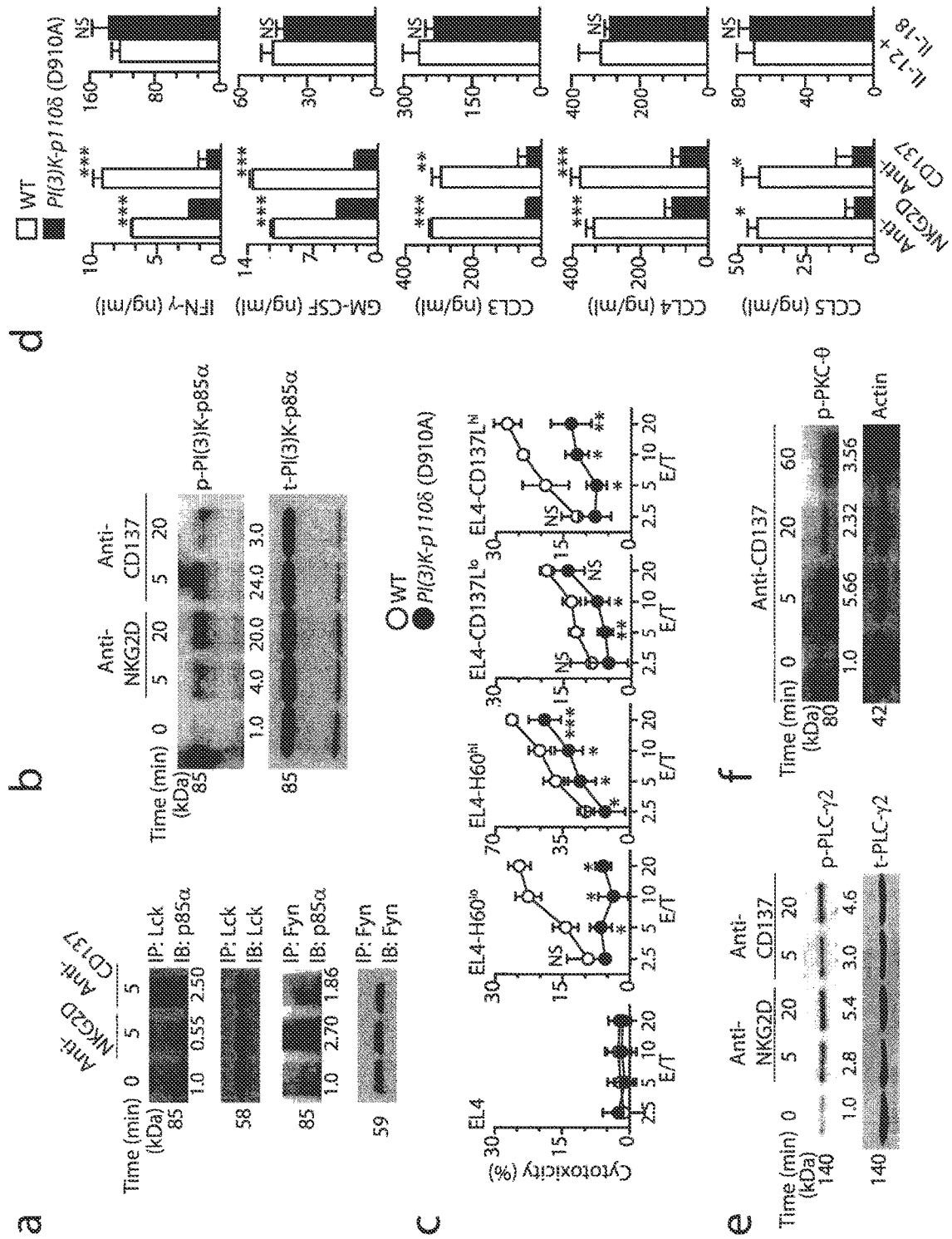
FIG. 4 presents data demonstrating that PI3K-p85α/p110δ is essential for cytotoxicity and cytokine production in NK cells. (a) Whole cell lysates from WT NK cells, un-stimulated or activated with plate-bound anti-NKG2D and anti-CD137 mAbs were immunoprecipitated for Lck (top) or Fyn (bottom) and probed with anti-PI3K-p85α antibody. Fyn and Lck were also analyzed following their respective immunoprecipitation. Fold induction was determined by densitometry following normalization to the respective protein that was immunoprecipitated. (b) Western blot analysis of phosphorylated and total PI3K-p85α following activation of WT NK cells with plate-bound anti-CD137 or anti-NKG2D mAb for the indicated time points. Fold induction was determined by densitometry, following normalization to total PI3K-p85α. (c) Average percent cytotoxicity of NK cells from WT (open circle) or $PI3K-p110δ^{D910A/D910A}$ (filled circle) against indicated target cells. (d) Quantitative analyses of cytokines and chemokines produced by WT (open) or $PI3K-p110δ^{D910A/D910A}$ (filled) NK cells following activation with plate-bound antibodies to NKG2D and CD137receptors. Cytokines and chemokines produced by NK cells in response to IL-12 and IL-18 stimulation are shown (right). c&d represent mean+std. dev., Student's t test *P<0.05, P<0.01, *P<0.001, NS, not significant versus WT NK cells. (e) Western blot indicating the phosphorylated and total PLC-γ2 following activation of WT NK cells with plate-bound anti-CD137 or anti-NKG2D mAbs. (f) Western blot indicating the phosphorylated PKC-θ following activation of WT NK cells with plate-bound anti-CD137 or anti-NKG2D mAbs. Actin was used as loading control. Fold induction in (e) and (f) was determined by densitometry, following normalization to total PLC-γ2 and actin, respectively. Data in a-f are representatives of at least three independent experiments. These results confirm the role of PI3 Kinase in regulating NK cell-mediated tumor lysis and inflammatory cytokine and chemokine production.
Figure 5:
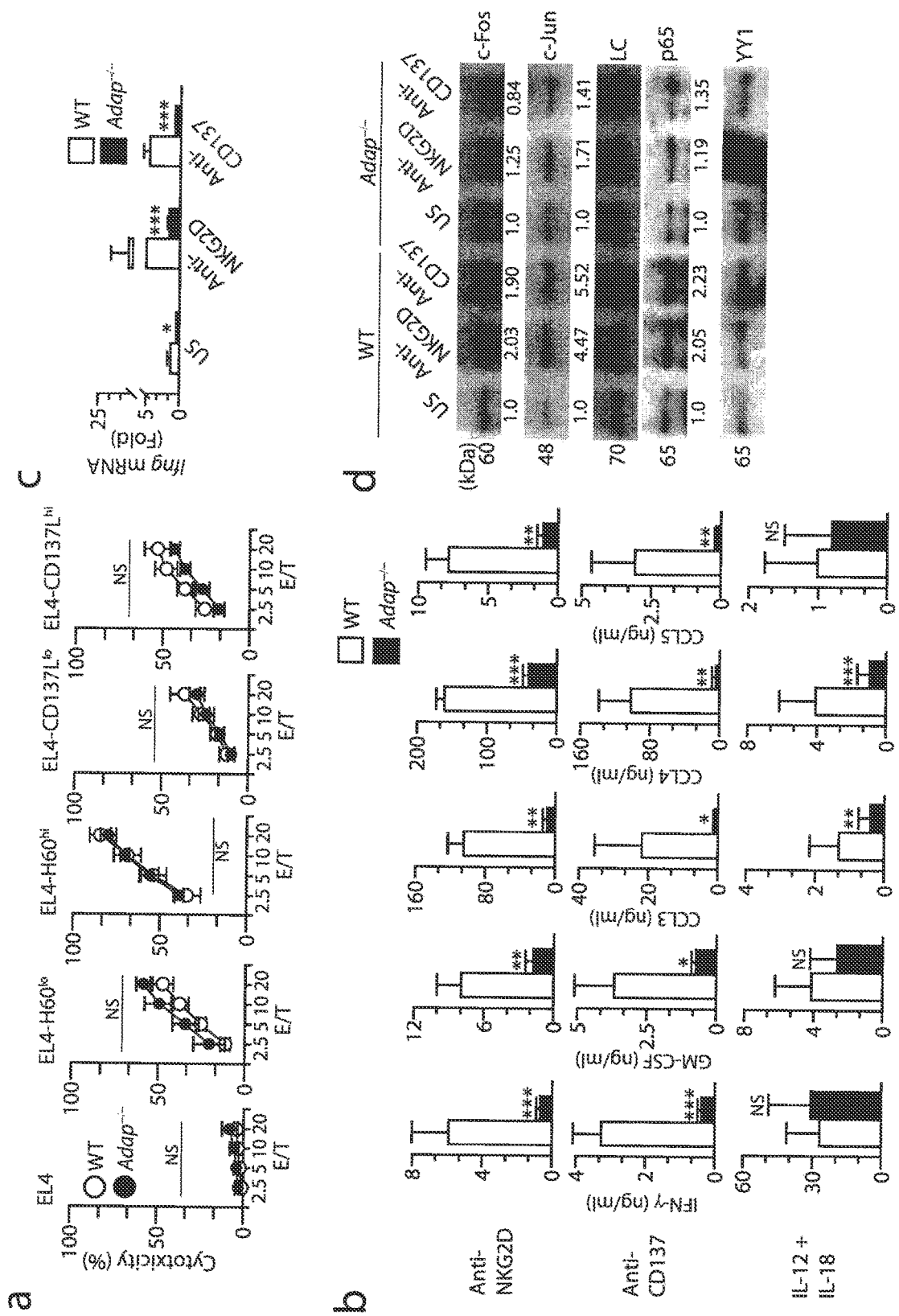
FIG. 5 demonstrates that ADAP is essential for cytokine production but not for cytotoxicity in NK cells. (a) ADAP expression in the WT and ADAP$^{-/-}$ NK cells was analyzed by western blot. Actin was used as a loading control. (b) Average percent cytotoxicity with standard deviation of NK cells from WT (open circles) or ADAP$^{-/-}$ (filled circles) mice. (c) Quantitative analyses of cytokines and chemokines produced by NK cells obtained from WT (open) or ADAP$^{-/-}$ (filled) mice following activation with plate-bound antibodies to NKG2D (top) and CD137 (middle) receptors using bioplex assay. Cytokines and chemokines produced by NK cells in response to IL-12 and IL-18 stimulation were also quantified (bottom). (d) Bar diagram representing the relative expression of FN-γ-encoding mRNA compared to GAPDH in WT (Open) and ADAP$^{-/-}$ (filled) NK cells left unstimulated or following NKG2D- or CD137-mediated activation. c&d represent mean+std. dev., Student's t test *P<0.05, P<0.01, *P<0.001, NS, not significant versus WT NK cells. (e) Immunoblot analyses of c-Fos, c-Jun and NF-κB p65 in the nuclear extracts isolated from WT and ADAP$^{-/-}$ NK cells stimulated under indicated conditions. Level of YY1 was used as internal loading control. A non-specific band obtained in the immunoblot when probed for c-Fos is also shown as loading control. Fold change in the nuclear c-Fos, c-Jun and NF-κB p65 in the WT and ADAP$^{-/-}$ NK cells following NKG2D- or CD137-mediated activation were calculated against their respective unstimulated controls. Data in a-e are representatives of at least three independent experiments. These results establish the critical role of ADAP in inflammatory cytokine and chemokine production but not in NK cell-mediated cytotoxicity.
Figure 6:
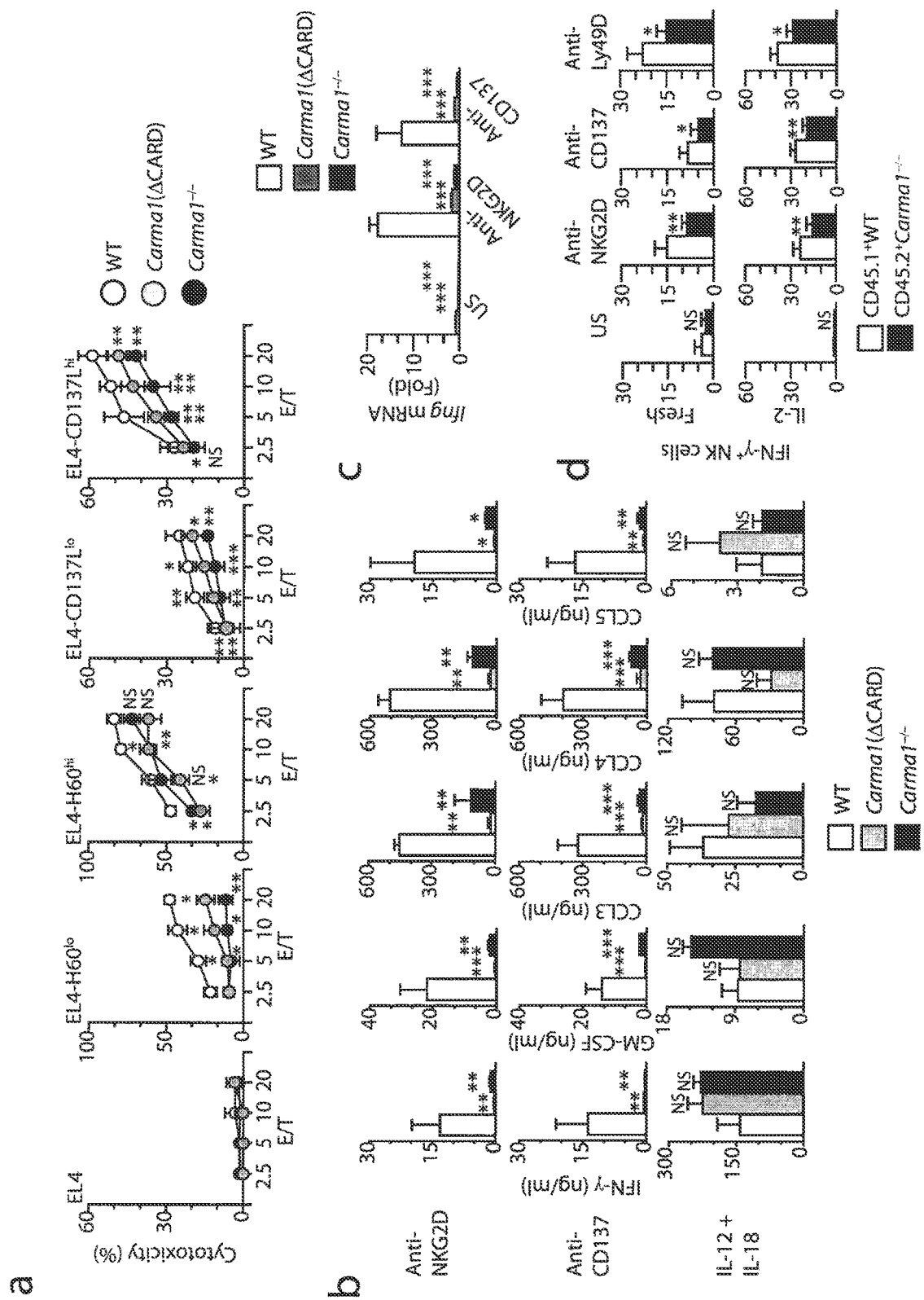
FIG. 6 illustrates that Carma1 is essential for cytotoxicity and cytokine production in NK cells. (a) Cytotoxic potentials of NK cells from WT (open circles), Carma1$^{\Delta CARD}$ (grey circles) or Carma1$^{-/-}$ (black circles) mice. Average percent cytotoxicity with standard deviations is shown. (b) Quantitative analyses of cytokines and chemokines produced by NK cells obtained from WT (open), Carma1$^{-/-}$ (black) or Carma1$^{\Delta CARD}$ (grey) mice following activation with plate-bound anti-NKG2D and anti-CD137 mAb using a bioplex assay system. Cytokines and chemokines produced by NK cells in response to IL-12 and IL-18-mediated stimulation are shown. (c) Bar diagram representing the relative expression of IFN-γ-encoding mRNA compared to GAPDH in WT (Open), Carma1$^{-/-}$ (black) or Carma1$^{\Delta CARD}$ (grey) NK cells left unstimulated or following NKG2D- or CD137-mediated activation. a-c represent mean+std. dev., Student's t test *P<0.05, P<0.01, *P<0.001, NS, not significant versus WT NK cells. (d) Bar diagram representing the percentage IFN-γ$^+$ fresh NK cells (top panel) or IL-2-cultured NK cells (bottom panel) in WT (CD45.1$^\square$, open histogram) and Carma1$^{-/-}$ (CD45.2$^\square$, black histogram) mice obtained from the spleen of irradiated and reconstituted Rag2cg$^{-/-}$ mice, one month after adoptive transfer of an equal mixture of WT and Carma1$^{-/-}$ bone marrow cells. Bar diagram represents mean+std. dev., Student's t test *P<0.05, P<0.01, *P<0.001, NS, not significant versus CD45.1$^+$ WT NK cells. Data in a-d are representatives of at least three independent experiments. These results demonstrate that signaling downstream of ADAP requires Carma1 protein.
Figure 7:
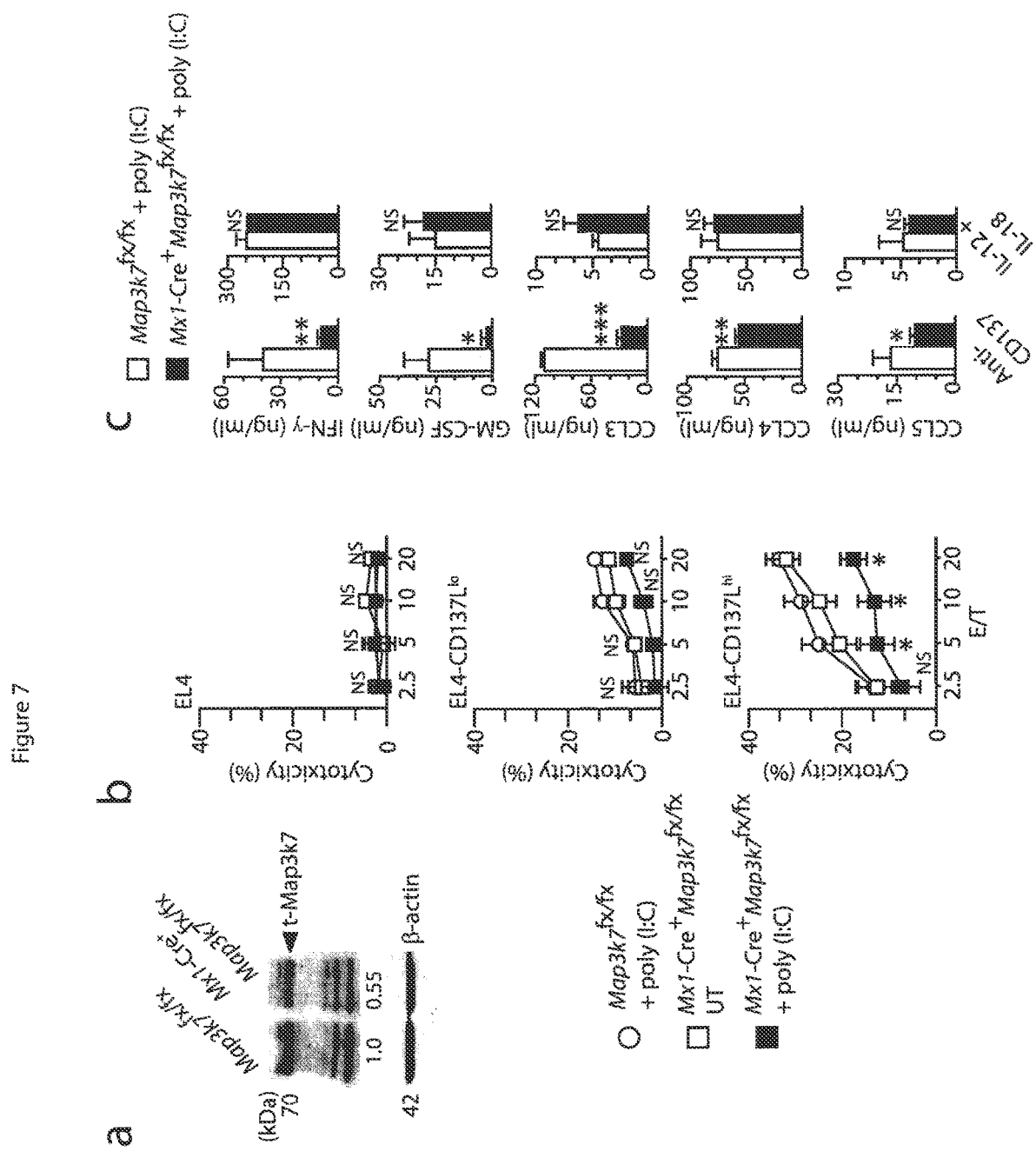
FIG. 7 illustrates that TAK1 links Carma1 to the CD137-mediated effector functions in NK cells. (a) Western blot showing the TAK1 expression level in IL-2-cultured NK cells obtained from poly (I:C)-treated TAK1$^{fx/fx}$ and Mx1Cre$^{+/+}$TAK1$^{fx/fx}$ mice. Actin expression was used as an internal loading control. Fold change in TAK1 expression was determined by densitometry following normalization with actin. (b) Average percent cytotoxicity with standard deviation of NK cells obtained from poly I:C-treated TAK1$^{fx/fx}$ mice (open circle) or from poly (I:C) untreated (open square) and treated (filled square) Mx1Cre$^{+/+}$TAK1$^{fx/fx}$ mice against the indicated targets, Student's t test *P<0.05, P<0.01, *P<0.001, NS, not significant versus NK cells from Mx1Cre$^{+/+}$TAK1$^{fx/fx}$ mice that were untreated with poly (I:C). (c) Quantitative analyses of cytokines and chemokines produced by NK cells derived from poly (I:C)-treated TAK1$^{fx/fx}$ (open) and Mx1Cre$^{+/+}$TAK1$^{fx/fx}$ (filled) mice following 18 h of activation with plate-bound anti-CD137 mAb (left) or with IL-12 and IL-18 (right). Student's t test *P<0.05, P<0.01, *P<0.001, NS, not significant versus NK cells from TAK1$^{fx/fx}$ mice that were treated with poly (I:C). Data in a-c are representatives of at least three independent experiments. These results demonstrate that signaling downstream of ADAP requires Tak1 protein.
Figure 8:
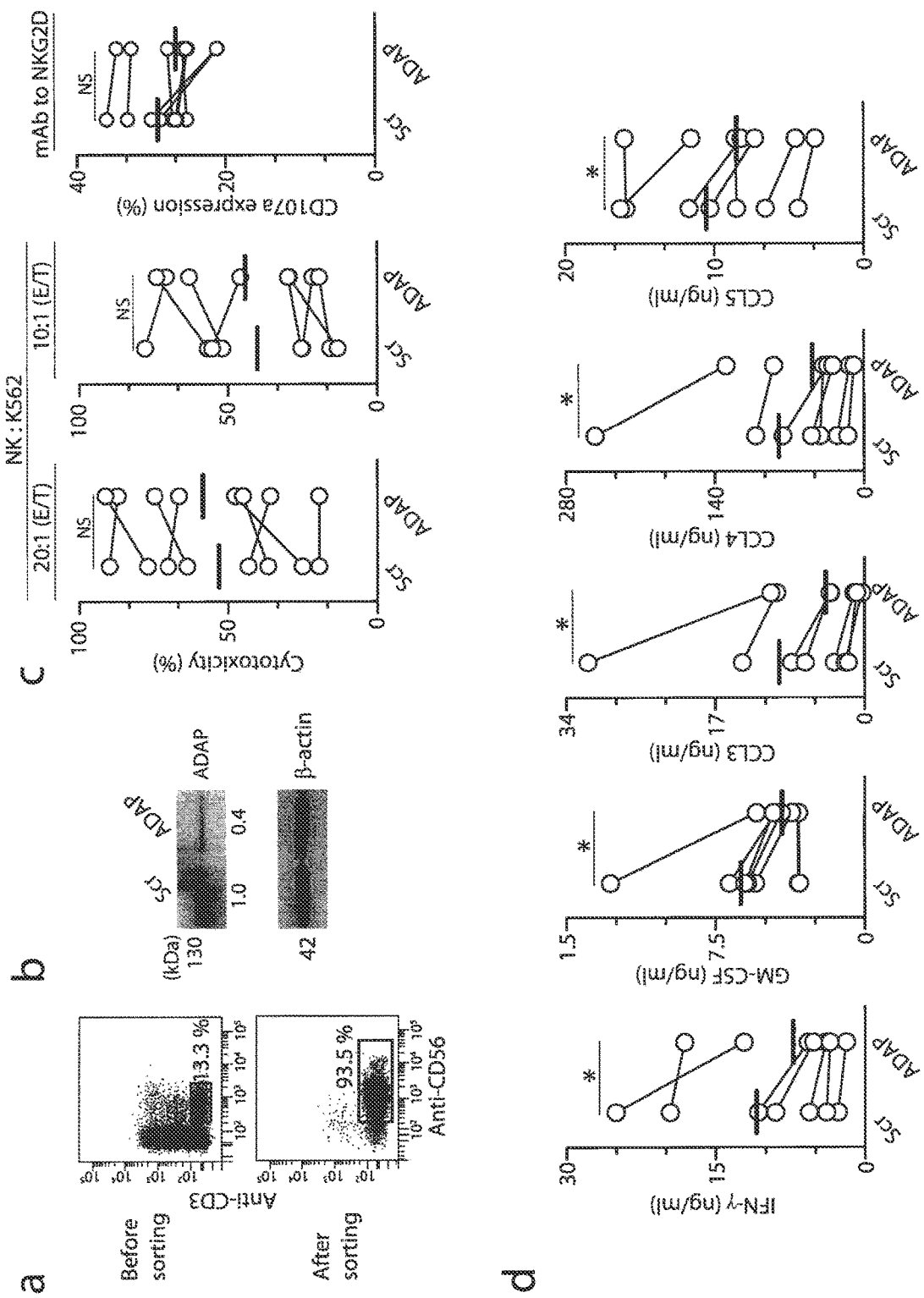
FIG. 8 presents data demonstrating that ADAP is essential for cytokine production but not for cytotoxicity in human NK cells. (a) Flow cytometry indicating the percentage CD3$^+$CD56$^+$ NK cells in total human PBMC (left) and in the cell fraction (right) obtained following negative selection for CD56$^+$ NK cells. Purified CD56$^+$ human NK cells were transfected with scrambled or ADAP-specific siRNA. (b) Western blot for ADAP in human NK cells that were transfected with scrambled or specific siRNA. Actin expression was used as an internal loading control. Fold change in ADAP expression was determined by densitometry following normalization with actin. (c) Dot plot represents the percentage CD56$^+$CD107$^+$ (left) and percentage CD56$^+$IFN-γ$^+$ (right) cells obtained following plate-bound anti-NKG2D-mediated activation of scrambled and ADAP-specific siRNA-transfected human NK cells, Student's t test *P<0.05, P<0.01, *P<0.001, NS, not significant versus NK cells treated with scrambled siRNA. Data in a-c are representatives of at least three independent experiments. These results establish the critical role of ADAP in inflammatory cytokine and chemokine production but not for cytotoxicity in human primary NK cells.
Figure 9:
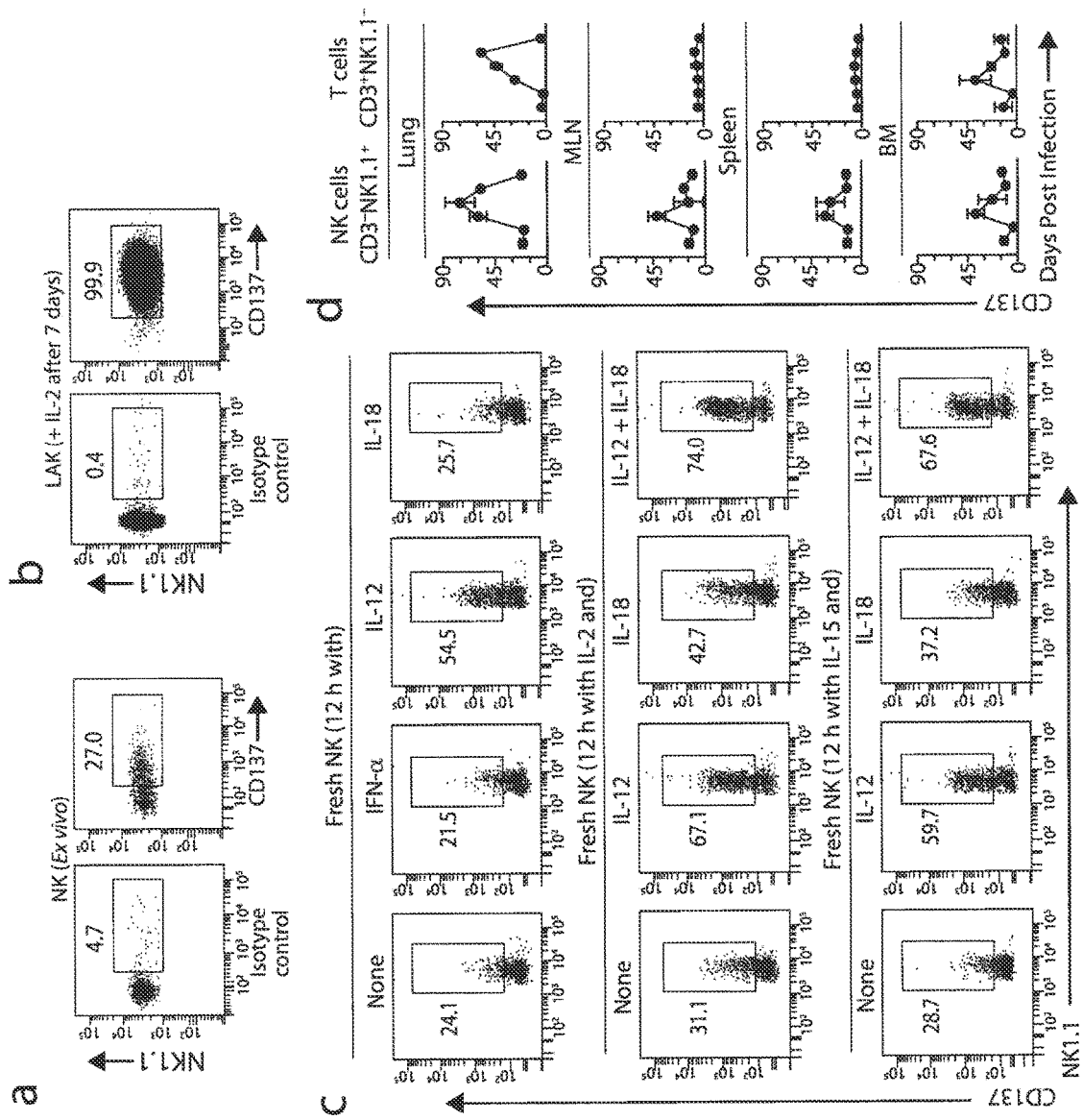
FIG. 9 presents data demonstrating that CD137 expression is inducible in splenic NK cells by cytokines and in the lung NK cells following influenza infection. (a) Flow cytometry analyses of CD137 expression in fresh splenic NK cells. Splenocytes from WT mice were gated for CD3$^-$NK1.1$^+$ NK cells and the percentage of NK cells that express CD137 are shown. Isotype staining is shown as control. (b) CD137 expression in splenic NK cells after 7 days in culture with IL-2. (c) CD137 induction in fresh NK cells following treatment with IFN-α, IL-12 and IL-18 alone (upper panels), in combination with IL-2 (middle panels), or IL-15 (bottom panels) for 12 h. WT mice were infected with H1N1-PR8 influenza virus (5000 pfu). (d) Time course of CD137 induction in CD3$^-$NK1.1$^+$NK cells and CD3$^-$NK1.1$^+$ T cells obtained from lung following influenza infection. a and b are representative of at least 10 mice. Data presented in c and d is a representative of at least three independent experiments. These results help to conclude that the expression of CD137 is regulated in NK cells.
Figure 10:
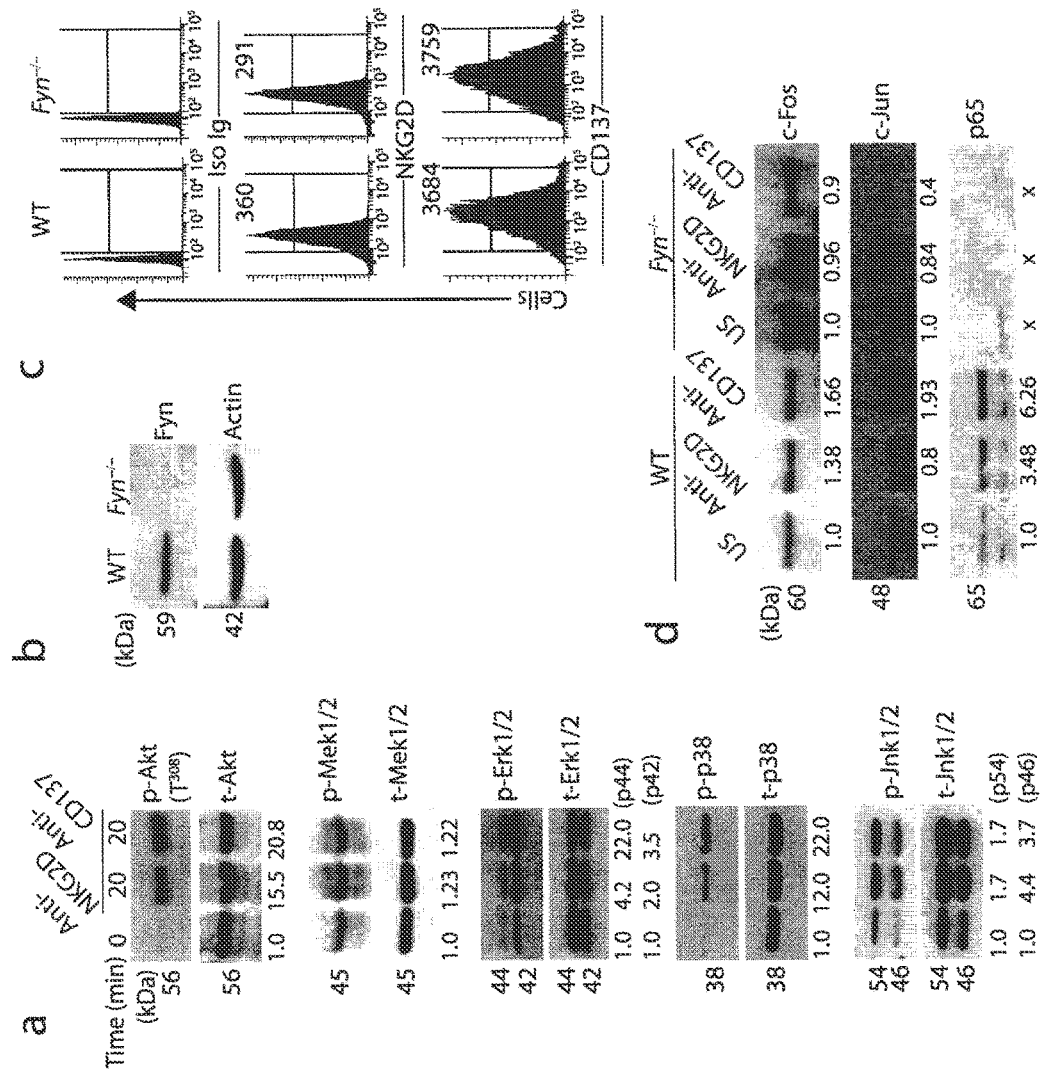
FIG. 10 presents data demonstrating that MAPK and transcription factor activation downstream of NKG2D and CD137. (a) Western blot analyses of AKT, MEK1/2, ERK1/2, p38 and JNK1/2 phosphorylation in WT NK cells following 20 m activation with plate-bound anti-NKG2D or anti-CD137 mAbs. Quantification of relative phosphorylation is shown at the bottom. (b) Flow cytometry analyses of NKG2D (middle) and CD137 (lower) expression in IL-2 expanded WT and Fyn$^{-/-}$ NK cells. Corresponding isotype controls are indicated (top). (c) Immunoblot analyses of c-Fos, c-Jun and NF-κB p65 in the nuclear extracts isolated from WT and Fyn$^{-/-}$ NK cells stimulated under indicated conditions. Fold change in the nuclear translocation of c-Fos, c-Jun and NF-κB p65 in the WT and Fyn$^{-/-}$ NK cells were calculated using unstimulated controls. X-denotes no detectable band intensity in unstimulated control. Data presented in a-c is a representative of at least three independent experiments. These results show that MAPK are activated downstream of NKG2D and CD137, which play an important role in NK cell activation.
Figure 11:
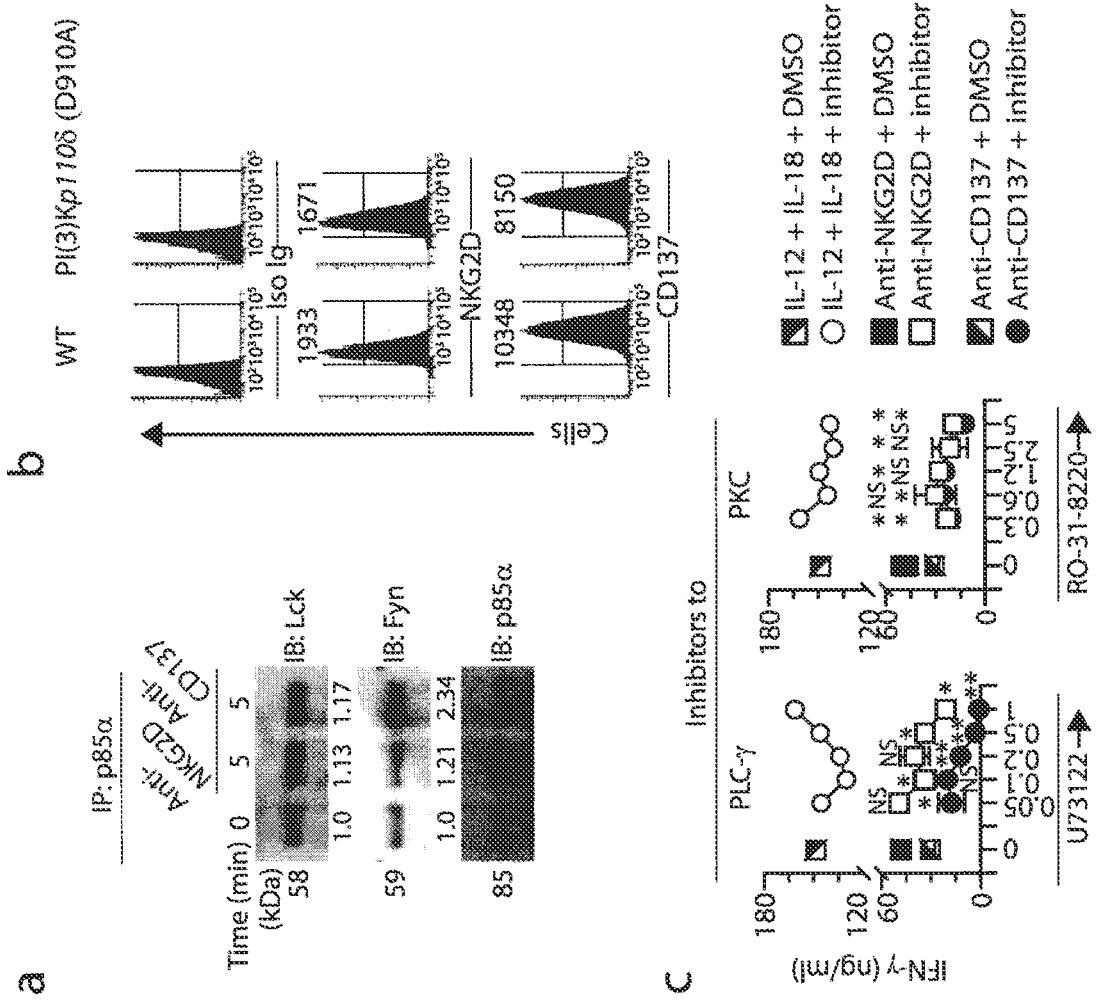
FIG. 11 presents. PI3 kinase plays a critical role in NKG2D and CD137-mediated cytokine production. (a) Whole cell lysates from WT NK cells were immunoprecipitated for PI3K-p85α following NKG2D or CD137-mediated activation. Unstimulated NK cells were used as controls. Membranes were probed for Lck and Fyn. Fold change was determined by densitometry, following normalization with the immunoprecipitated protein, p85α. (b) Flow cytometry analyses of CD137 expression (right) in IL-2-expanded WT and PI3K-p110δ$^{D910A/D910A}$ NK cells. Mean fluorescence intensity of the corresponding isotype control (left) is also shown. (c) ELISA-based quantification of IFN-γ following plate-bound anti-CD137 mAb-mediated activation in WT NK cells pre-treated with inhibitor (filled circles) for PLC-γ2, U73122 (left; 1, 0.5, 0.25, 0.125, 0.05 μM) or PKC inhibitor, RO-31-8220 (right; 10, 5, 2.5, 1.25, 0.625 μM). Untreated (squares) and IL-12+IL-18-activated (open circles) NK cells are shown as controls. (Mean+std. dev., Student's t test *P<0.05, P<0.01, *P<0.001, NS, not significant versus respective mAb-stimulated and DMSO (vehicle)-treated NK cells. Data in a-d are representatives of at least three independent experiments. These results confirm the role of PI3 Kinase in regulating NK cell-mediated tumor lysis and inflammatory cytokine and chemokine production.
Figure 12:
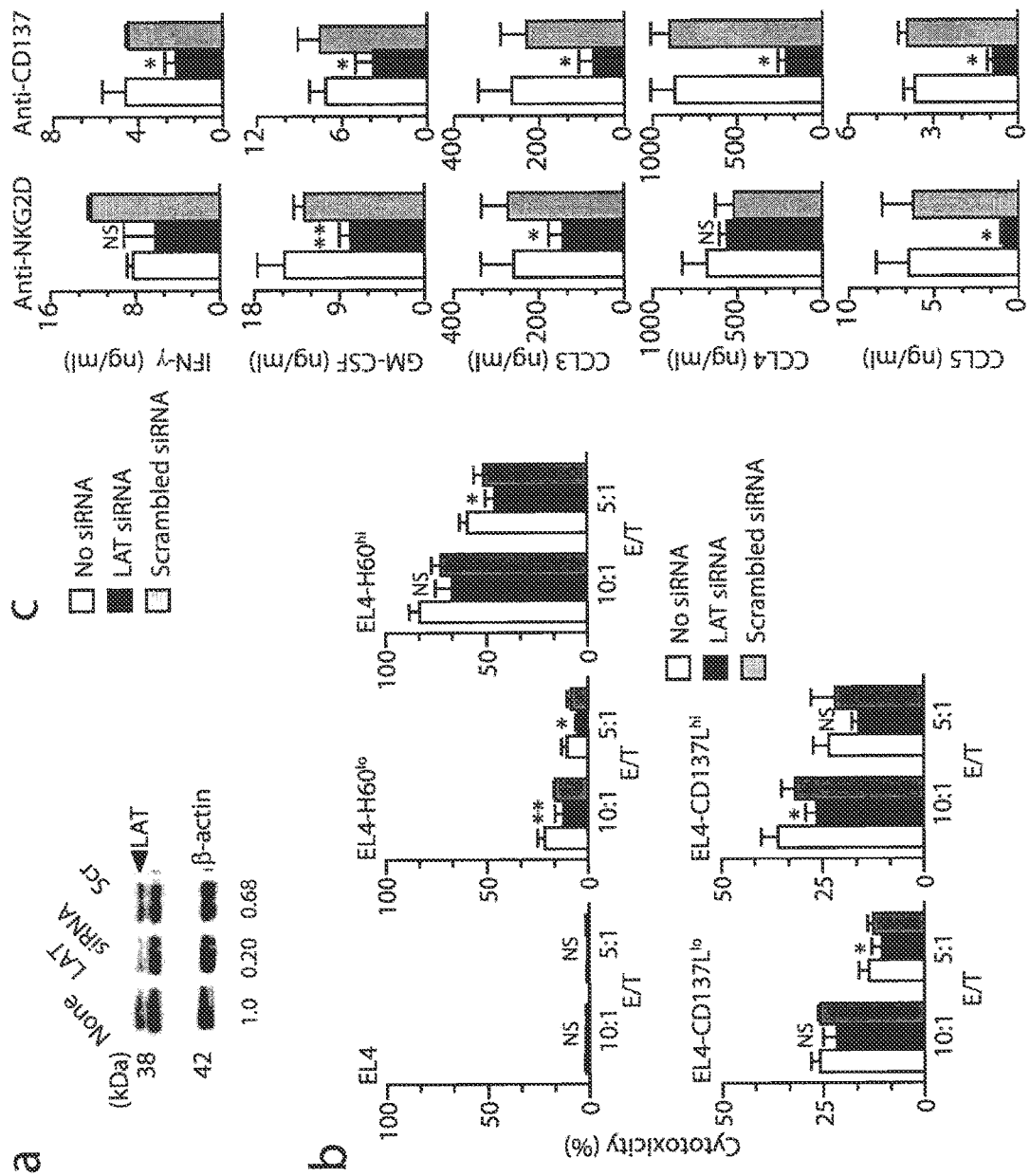
FIG. 12 presents data demonstrating that LAT is essential for NK cell effector functions. (a) Western blot for LAT in NK cells following mock, LAT-specific and scrambled siRNA transfections. Actin expression was used as an internal loading control. Fold change in LAT expression was determined by densitometry following normalization with corresponding actin band intensity. (b) Bar diagram represents the average percent cytotoxicity with standard deviation of NK cells transfected with mock (open), LAT-specific siRNA (black) or scrambled siRNA (grey) against indicated target cells. (c) Bar diagram represents the quantitative analyses of cytokine and chemokine production following anti-NKG2D- and anti-CD137 mAb-mediated activation of WT splenic NK cells that were transiently transfected with mock, LAT-specific or scrambled siRNA. Data presented in b&c are averages with standard deviations. (Mean+std. dev., Student's t test *P<0.05, P<0.01, *P<0.001, NS, not significant) Data in a-d are representatives of at least three independent experiments. These findings establish the role of scaffold protein LAT in both NK cell-mediated cytotoxicity and inflammatory cytokine and chemokine production.
Figure 13:
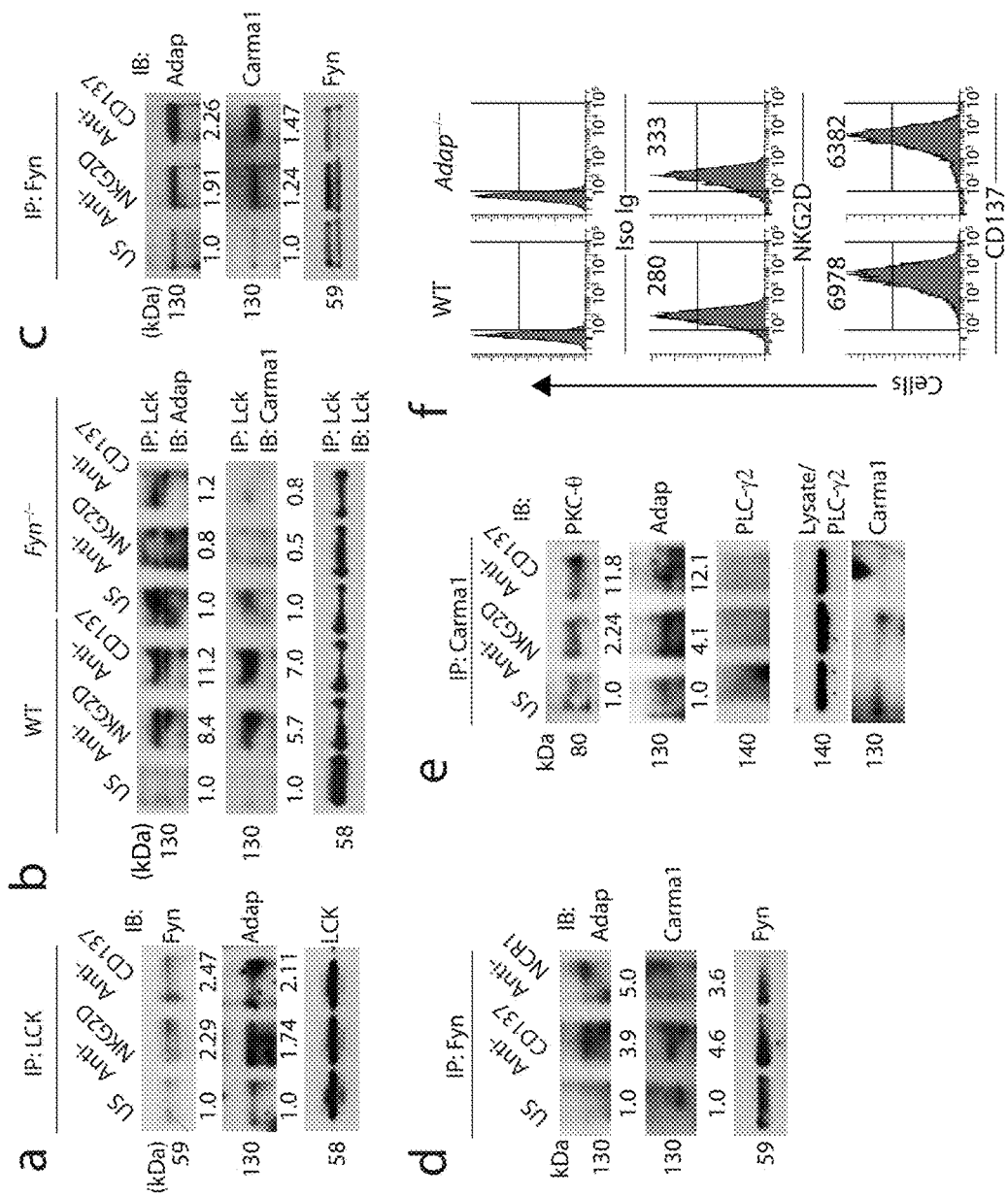
FIG. 13 presents data demonstrating that ADAP-mediated signaling events in NK cells is essential for cytokine production but not for cytotoxicity. (a) Whole cell lysates from WT NK cells, unstimulated or activated with plate-bound anti-NKG2D and anti-CD137 mAbs were immunoprecipitated for Lck and probed for Fyn and ADAP. Fold change was determined by densitometry, following normalization with the immunoprecipitated protein, Lck. (b) Whole cell lysates from unstimulated, NKG2D- or CD137-stimulated WT NK cells were immunoprecipitated for Fyn and probed for ADAP and Carma1. (c) Whole cell lysates from unstimulated, CD137- or NCR1-stimulated WT NK cells were immunoprecipitated for Fyn and probed for ADAP and Carma1. (d) In a similar experiment, whole cell lysates were immunoprecipitated for Carma1 and probed for PKC-θ, ADAP and PLC-γ2. In a, b, c & d, fold induction was determined by densitometry following normalization to the protein that was immunoprecipitated. (e) Flow cytometry analyses of NKG2D (middle) and CD137 (bottom) expression in IL-2-cultured NK cells obtained from WT (left) and ADAP$^{-/-}$ (right) mice. Mean fluorescence intensity of the corresponding isotype control (top) is shown. Data in a-e are representatives of at least three independent experiments. These results establish the critical role of ADAP in inflammatory cytokine and chemokine production but not in NK cell-mediated cytotoxicity.
Figure 14:
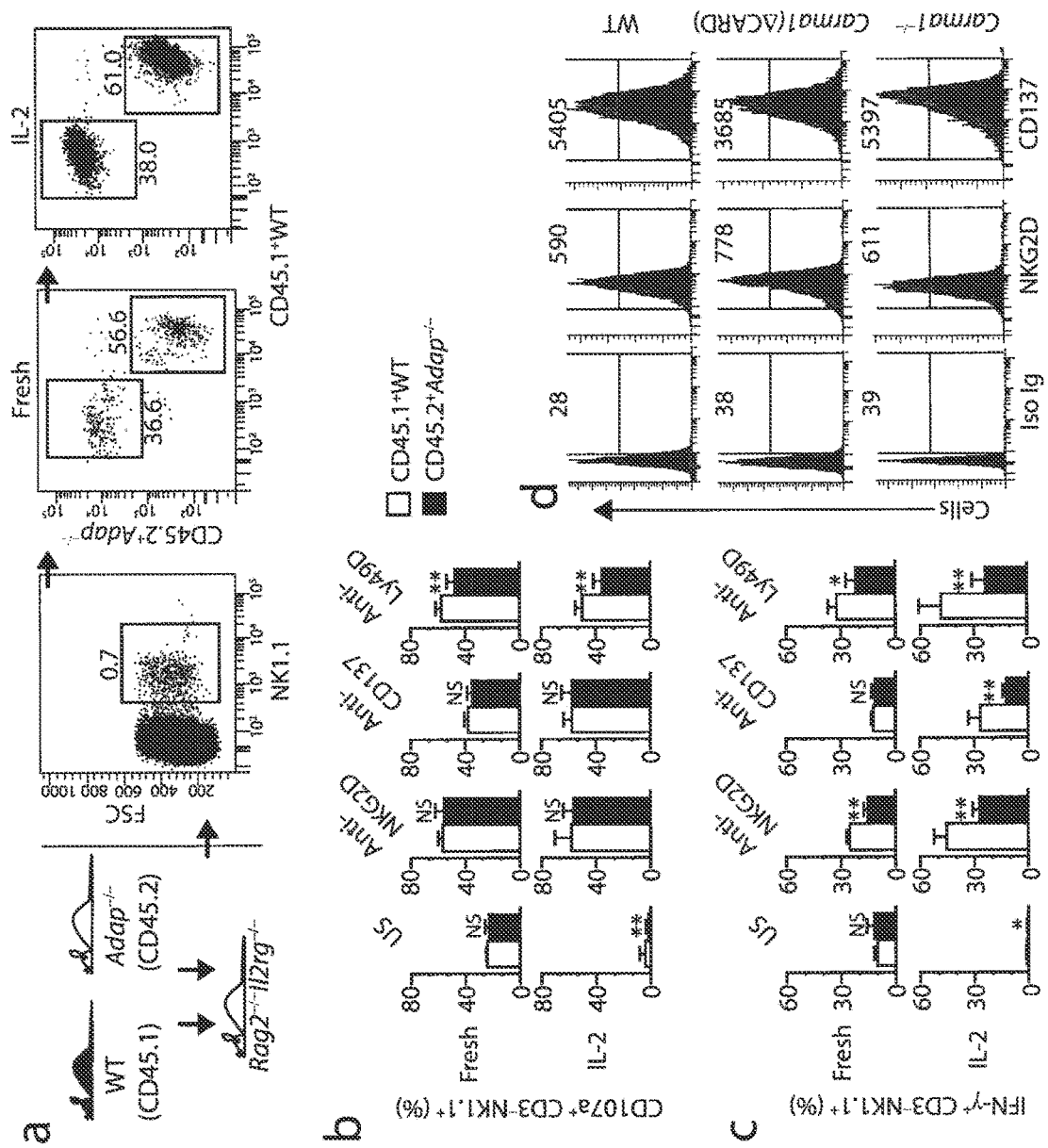
FIG. 14 presents. ADAP recruits Carma1 to the signaling complex following NKG2D, CD137, and NCR1-mediacted activation of NK cells. (a) Adoptive transfer experiments were performed to confirm the role of ADAP in NK cell-mediated cytokine production but not cytotoxicity. Bone marrow cells from WT (CD45.1$^+$) and ADAP$^{-/-}$ (CD45.2$^+$) mice were mixed in equal ratio and injected into irradiated Rag2$_c$γ$^{-/-}$ mice. One month after adoptive transfer, spleens were collected from these mice. The existence of NK1.1$^+$ WT (CD45.1$^+$) and ADAP$^{-/-}$ NK cells in the reconstituted spleen following irradiation and adoptive transfer was confirmed by flow cytometry. NK cells were also enriched from the remaining portion of the splenocytes by passing them through nylon wool. The enriched NK cells were cultured with IL-2 for 7 days. The existence of WT (CD45.1$^+$) and ADAP$^{-/-}$ (CD45.2$^+$) NK cells in the IL-2 cultured cell fraction was also analyzed by flow cytometry. (b) The efficiency of fresh WT and ADAP$^{-/-}$ NK cells to mediate cytotoxicity was analyzed by initially culturing them overnight with IL-2 and then activating them with plate-bound anti-NKG2D, anti-CD137 and anti-Ly49D mAbs. The IL-2 cultured NK cells were also stimulated in a similar fashion. Bar diagram represents the percentage CD107a$^+$ fresh (top panel) or IL-2-cultured (bottom panel) WT (CD45.1$^+$, open histogram) and ADAP$^{-/-}$ (CD45.2$^+$, black histogram) NK cells, either left unstimulated or activated with the indicated plate-bound antibodies. (c) A similar analysis was performed to analyze cytokine production in fresh and IL-2 cultured WT and ADAP$^{-/-}$ NK cells. Bar diagram represents the percentage IFN-γ$^+$ fresh (top panel) or IL-2-cultured (bottom panel) WT (CD45.1$^+$, open histogram) and ADAP$^{-/-}$ (CD45.2$^+$, black histogram) NK cells, either left unstimulated or activated with the indicated plate-bound antibodies, (b&c represent mean+std. dev., Student's t test *P<0.05, P<0.01, *P<0.001, NS, not significant, versus CD45.1$^+$ WT NK cells.) (d) Flow cytometry analyses of NKG2D (middle) and CD137 (right) expression in IL-2-cultured NK cells from WT, Carma1$^{-/-}$ and Carma1$^{\Delta CARD}$ mice. Mean fluorescence intensity of the corresponding isotype control (left) is also indicated. Data in a-d are representatives of at least three independent experiments. These observations prove that ADAP requires Carma1 in order to produced inflammatory cytokines and chemokines.
Figure 15:
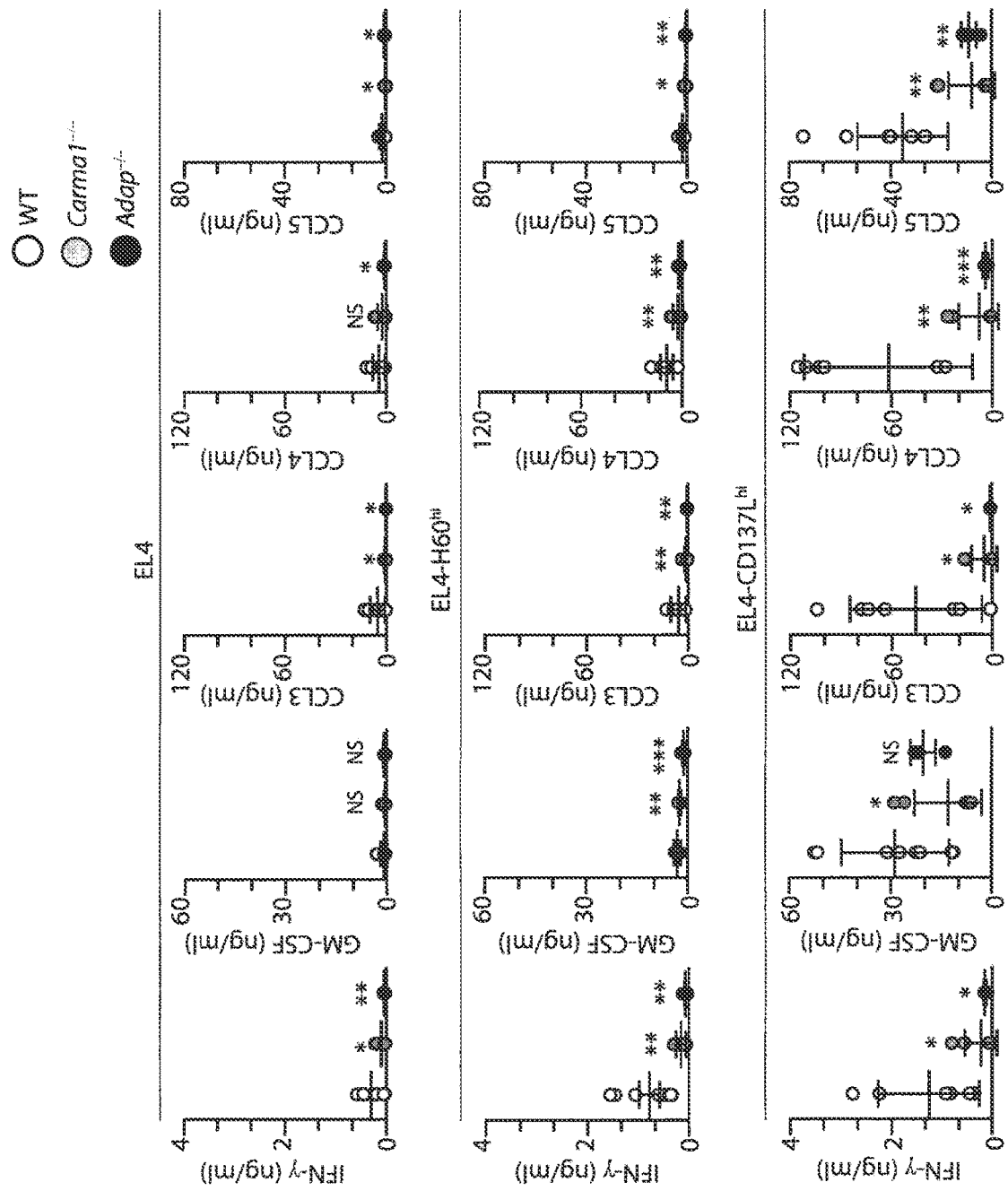
FIG. 15 demonstrates cytokine production in response to H60 and 4-1BBL expressing tumor cells is abrogated in Carma1$^{-/-}$ and ADAP$^{-/-}$ NK cells. IL-2-cultured NK cells from WT, Carma1$^{-/-}$ and ADAP$^{-/-}$ mice were co-cultured with the parental EL4, EL4$^{H60-Hi}$ or EL4$^{4-1BBL-Hi}$ stable cell lines. The quantity of cytokines/chemokines in the culture supernatant was determined using a bioplex assay. Panel indicates the various cytokines produced in response to EL4
Figure 16:
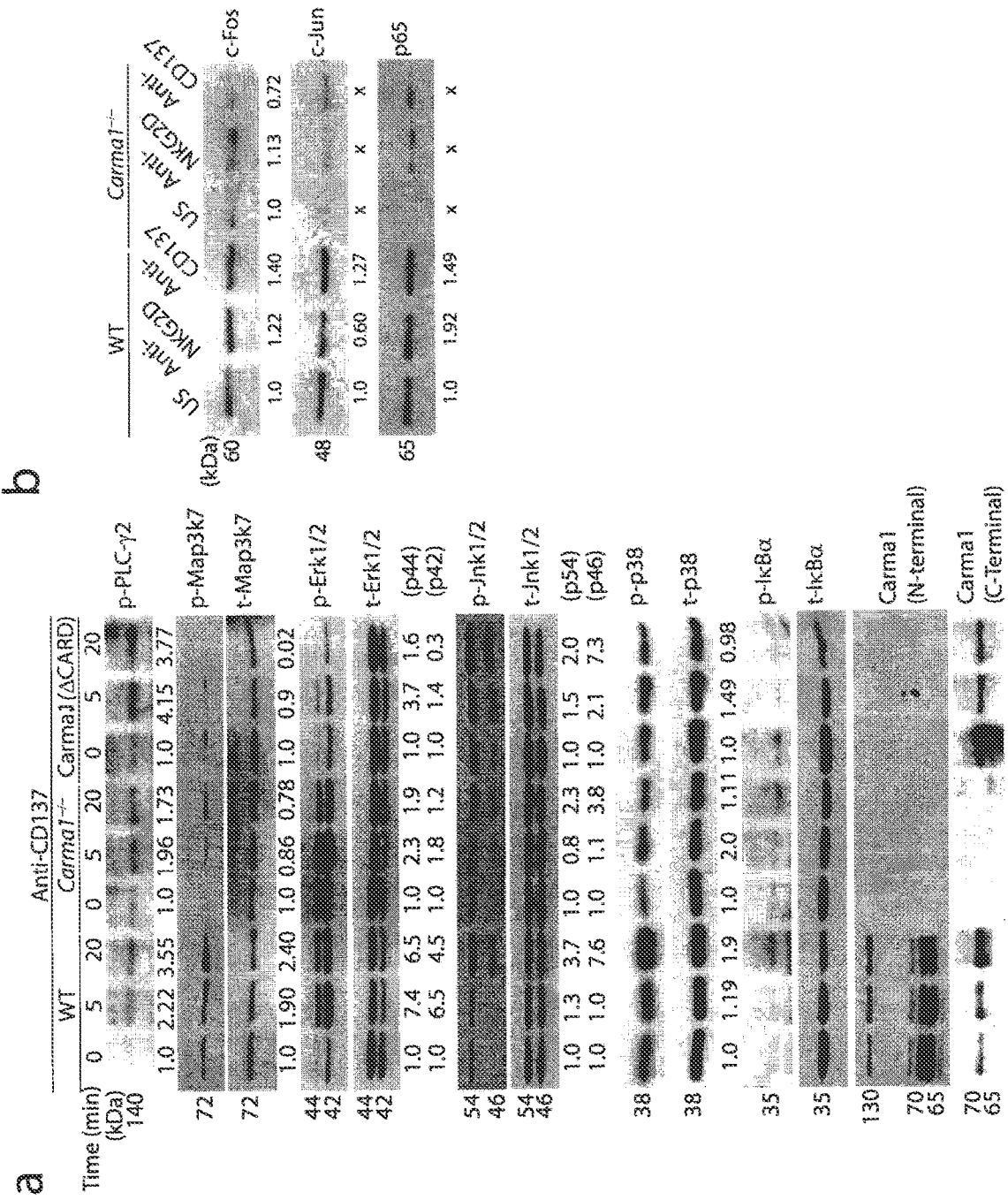

FIG. 16 illustrates that Carma1 is essential for TAK1 activation and nuclear translocation of c-Fos, c-Jun and NF-κB p65. (a) Western blot showing the phosphorylation of PLC-γ2, TAK1, ERK1/2, JNK1/2, p38 and IκBα in NK cells obtained from WT, Carma1$^{-/-}$ or Carma1$^{\Delta CARD}$ mice following plate-bound anti-CD137-mediated activation for the indicated time points. Fold change in phosphorylation between the unstimulated and activated NK cells was determined by densitometry, following normalization to the corresponding total proteins. A major portion of the full-length Carma1 is cleaved into two fragments (~70 and 65 kDa) in NK cells. Therefore, membranes were also probed for Carma1 using a rabbit mAb against a peptide corresponding to residues surrounding threonine$^{175}$ in the N-terminus of Carma1 and a goat polyclonal antibody raised against the C-terminal 1131-1147 residue of the human protein. (b) Immunoblot analyses of c-Fos, c-Jun, and NF-κB p65 in the nuclear extracts isolated from WT and Carma1$^{-/-}$ NK cells. Fold change in the nuclear translocation of c-Fos, c-Jun, and NF-κB p65 in the WT and Carma1$^{-/-}$ NK cells were calculated using their respective unstimulated controls. X-denotes no detectable band intensity in unstimulated control. Data in a and b are representatives of at least three independent experiments. (c) A schematic representation of the signaling events that are set forth following engagement of the activating receptors NKG2D or CD137 on the surface of NK cells. Based on our findings, the prominent signaling events culminate in cytotoxicity while those that lead to cytokine production are clearly demarcated, This set of data demonstrate that ADAP via Carma1 connects to TAK1 to regulate NK cell effector functions.

DETAILED DESCRIPTION OF THE INVENTION

The present invention is based, at least in part, on Applicants' discovery that ADAP has an exclusive role in the production of inflammatory cytokines and chemokines, but is not required to mediate target cell (e.g., tumor cell) cytotoxicity. Multiple autoimmune diseases and other immunological disorders are caused by an uncontrolled production of inflammatory cytokines and chemokines, and excessive inflammatory cytokine release is associated with severe health complications. Examples of diseases for which control of inflammatory cytokine production can be beneficial include cancers, allergies, any type of infection, toxic shock syndrome, sepsis, any type of autoimmune disease, arthritis, Crohn's disease, lupus, psoriasis, or any other disease for which the hallmark feature is toxic cytokine release that causes deleterious effects in a subject. As described herein, Applicants identified CD137 as an independent activation receptor in Natural Killer (NK) cells and, importantly, defined unique signaling recruitments that produce inflammatory cytokines and cytotoxicity in NK cells.

It is known by those having ordinary skill in the art that CD137 is expressed in T cells, dendritic cells, and other immune cells. Downstream of CD137, Lck, and Fyn initiate at least two distinct pathways. In the first pathway, PI3K-p85α recruitment leads to the production of PIP$_3$ and activation of PLC-γ2, which in turn initiates the production of DAG and IP3 and, subsequently, activates PKC-θ, leading to phosphorylation and activation of Carma1 and assembly of the CBM signalosome. Also, PI3K could regulate the CBM signalosome formation via the activation of PDK1. Most importantly, PI3K-p85α/p110δ could also be a critical factor in Ras-GTP-dependent PAK1→C-Raf→MEK1/2→ERK1/2 activation. In this context, it is important to note that activation of ERK1/2 is required for degranulation. Thus, a catalytically inactive PI3K-p110δ could have impaired both cytotoxicity (via ERK1/2) and cytokine production (via the CBM signalosome/NF-κB and AP1).

The CD137 receptor was used to demonstrate that cytoplasmic signaling molecules have distinct roles with regard to cytotoxicity (e.g., selectively targeting cells for death) and to cytokine production. It was observed that, in chimeric cells, CD137-mediated activation initiates a novel, second pathway through Lck/Fyn/ADAP molecules that uniquely engage the Carma1/Bcl10/Malt1/TAK1 signalosome. Downstream of CD137, Fyn binds to ADAP with high affinity, leading to the recruitment of a Carma1/Bcl10/Malt1/TAK1 complex that is exclusively responsible for inflammatory cytokine production. Thus, absence of ADAP resulted in a failure of the CBM signalosome and thereby non-activation of NF-κB and AP1. Although recent studies have shown that TAK1 can directly bind to ADAP, this interaction does not rescue the production of cytokines in Carma1$^{-/-}$ or Carma1$^{\Delta CARD}$ NK cells, strongly suggesting that a fully functional CBM signalosome is obligatory for cytokine production but not for cytotoxicity.

Applicants have provided the first detailed blueprint of signaling molecules downstream of CD137 or NKG2D and identified potential therapeutic targets to exclusively minimize inflammatory cytokine production in patients undergoing NK or CD8$^+$ T cell-mediated immunotherapy. While loss of ADAP function has no effect on CD137 or NKG2D mediated NK cell cytotoxicity, it significantly reduces production of inflammatory cytokines and chemokines such as IFN-γ, GM-CSF, MIP-1α, MIP1β, and RANTES. These data demonstrate the potential to target certain signaling molecules in NK and T cells to significantly reduce or prevent toxic release of inflammatory cytokines without compromising the efficacy of the immune cell's cytotoxicity against tumors and other targets.

Accordingly, one aspect of the present invention relates to cytotoxic immune cells (e.g., NK cells or T cells) comprising chimeric antigen receptors (CARs) whereby the cells retain their cytotoxic function but are capable of reducing inflammatory ("toxic") cytokine production. As used herein, the term "cytokine" refers to cytokines (e.g., interferon gamma, granulocyte macrophage colony stimulating factor, tumor necrosis factor alpha), chemokines (e.g., MIP 1 alpha, MIP 1 beta, RANTES), and other soluble mediators of inflammation, such as reactive oxygen species and nitric oxide. A method of the present invention includes, therefore, providing NK cells or T cells comprising a manipulated chimeric antigen receptors to decrease toxic cytokine release or "cytokine release syndrome" in the subject. As used herein, decreasing toxic cytokine release or toxic cytokine levels refers to reducing or attenuating toxic cytokine levels in a subject, or attenuating, eliminating, or reducing the likelihood or incidence of cytokine release syndrome in a subject.

Immune cells having a modified chimeric antigen receptor can comprise one or more modifications in a nucleic acid sequence (e.g., deletion, substitution) or an amino acid sequence encoding a polypeptide. In some cases, a chimeric antigen receptor comprises one or more specific modifications in an amino acid sequence encoding a variable region of a tumor specific antibody such as, without limitation, anti-CD19. In other cases, a chimeric antigen receptor comprises one or more specific modifications in an amino acid sequence encoding a cytoplasmic domain of a polypeptide such as CD3ζ; CD28, and CD137. As used herein, the phrase "substantially unchanged" refers to a level (e.g., of activity) which remains at least 80%, and preferably at least 90%, of the initial level of cytotoxicity or a level of cytotoxicity of an immune cell not modified to express a chimeric antigen receptor. Accordingly, a substantially unchanged level of cytotoxicity for a modified immune cell may not be exactly the same as that of an unmodified immune cell but is at least 80% or at least 90% of the unmodified cell's cytotoxicity level. Any appropriate method of quantifying cytotoxicity can be used to determine whether activity in an immune cell modified to express a CAR remains substantially unchanged. For example, cytotoxicity can be quantified using a cell culture-based assay such as the cytotoxic assays described in the Examples. Cytotoxicity assays can employ dyes that preferentially stain the DNA of dead cells. In other cases, fluorescent and luminescent assays that measure the relative number of live and dead cells in a cell population can be used. For such assays, protease activities serve as markers for cell viability and cell toxicity and a labeled cell permeable peptide generates fluorescent signals that are proportional to the number of viable cells in the sample. Kits for various cytotoxicity assays are commercially available from manufacturers such as Promega and Life Technologies.

The present invention provides methods for reducing or preventing cytokine production in a subject. A method for reducing or preventing cytokine production or toxic cytokine release can comprise providing to a subject a cytotoxic cell that has been genetically modified to express a CAR. In some cases, a genetically modified cytotoxic cell comprises a CAR having at least two elements. A first element is an extracellular receptor that recognizes and specifically binds to a particular ligand or antigen of interest. The first element would act to target the cytotoxic cell to kill the cell types of interest. First elements could include but are not limited to cluster of differentiation (CD) cell surface proteins or "markers" or CD marker receptors specific to the cell type of interest, a receptor for a tumor-derived peptide, a receptor for a viral or bacterial antigen on a cell surface, or another type of receptor for a cell surface. Examples of first elements could include but are not limited to receptors for CD19 or CD20 to target B cells in the case where one would like to destroy B cells as in leukemia. Other examples of first elements could be receptors for antigens such as ROR1, CD22, or GD2. In such cases, the first element can specifically bind to a CD19, CD20, CD22, ROR1, or GD2 antigen.

The second element is a signaling moiety that initiates cytotoxic and other responses of the cell. In some cases, the signaling moiety comprises a CD137, CD3ζ, CD28, or a NKG2D cytoplasmic tail. A signaling molecule can comprise at least a portion of an ADAP polypeptide or Fyn polypeptide in a form that can either be anchored to the CAR or be released into the cell cytoplasm. Exemplary signaling moieties for the second element include those polypeptides which are releasable into the cell cytoplasm as "decoy polypeptides" and are able to compete for a binding site against either Fyn or ADAP in such a way as to impede ADAP signaling. A decoy polypeptide of ADAP, for example, would compete for binding with the normal Fyn available in the cell but not allow for further recruitment of Carma1 and Tak1 and the later cytokine release. Another exemplary second element could include the signaling moiety with an additional internal ribosome entry site (IRES) sequence prior to a sequence encoding an ADAP or Fyn polypeptide so that said polypeptide is expressed as a separate peptide within the genetically modified cell. IRES sequences can be used to express additional separate proteins within a viral or retroviral construct. The separate peptide would then be able to interact with either ADAP or Fyn so that production of cytokines is prevented. Such a polypeptide serves as a decoy polypeptide by binding to either ADAP or Fyn, thereby decreasing cytokine release from the cytotoxic cell relative to a cytotoxic cell not genetically modified to generate such a peptide.

Decoy polypeptides of signaling moieties described herein can be expressed as polypeptide chains that can be released from a CAR when it is activated and act to inhibit downstream signaling mediated by ADAP or Fyn. For example, an IRES sequence can be incorporated into a nucleic acid encoding a decoy protein in a genetically modified immune cell that may additionally include a CAR. In some cases, a decoy polypeptide comprises at least 3 contiguous amino acids selected from ADAP residues such as 600-630 of SEQ ID NO:1. Preferably, the at least three amino acids are selected from residues 609-620 of SEQ ID NO:1. In other cases, a decoy polypeptide comprises at least 3 contiguous amino acids selected from residues 619-630 of SEQ ID NO:1. Preferably, the at least 3 contiguous amino acids selected from residues 619-630 of SEQ ID NO:1. A decoy polypeptide can comprises at least 3 contiguous amino acids of an amino acid sequence selected from the group consisting of SEQ ID NOS:1, 2, and 3.

In some cases, a decoy polypeptide comprises at least 3 contiguous amino acids selected from SEQ ID NO:2 (human Fyn). Preferably, the at least three amino acids are selected from the residues of Fyn which interact with residues 609-620 of SEQ ID NO:1 (human ADAP). In other cases, a decoy polypeptide comprises at least 3 contiguous amino acids selected from the residues of Fyn which interact with residues 600-640 of SEQ ID NO:1 (human ADAP). Preferably, the at least 3 contiguous amino acids are selected from residues which interact with 619-630 of SEQ ID NO:1.

In some cases, a decoy polypeptide comprises at least one conservative amino acid substitution relative to an unmodified amino acid sequence. In other cases, the decoy polypeptide comprises a non-conservative amino acid substitution. In such cases, decoy polypeptides having such modifications exhibit increased stability or a longer half-life relative to a decoy polypeptide lacking such an amino acid substitution.

In some cases, genetically modified cytotoxic cells are autologous to the subject to which they are provided. Cytotoxic cells for genetic modification can be obtained from bone marrow of the subject or a donor. In other cases, the cells are obtained from a stem cell. For example, cytotoxic cells can be derived from human pluripotent stem cells such as human embryonic stem cells or human induced pluripotent cells. In the case of induced pluripotent stem cells (IPSCs), such pluripotent cells can be obtained using a somatic cell from the subject to which genetically modified cytotoxic cells will be provided. As described herein, methods for obtaining immune cells from a subject or donor can include harvesting cells by venipuncture, by apheresis methods, by white cell mobilization followed by apheresis or venipuncture, or by bone marrow aspiration.

By way of example, chimeric antigen receptors appropriate for use according to a method provided herein have specificity for a subset of immune cells, specificity for one or more tumor antigens, or specificity for one or more viral antigens.

A further aspect of the present invention relates to immunotherapy methods for reducing inflammatory ("toxic") cytokine production. For example, a method for reducing toxic cytokine production can comprise a step of providing immune cells to a subject, where the immune cells (e.g., NK cells, T lymphocytes) are specifically modified to express a chimeric antigen receptor (CAR). Modified CAR-expressing immune cells useful for the presently provided invention exhibit reduced inflammatory cytokine or chemokine release but do not exhibit substantially altered cytotoxicity. Any appropriate method of providing modified CAR-expressing immune cells to a subject can be used for methods described herein. In exemplary embodiments, methods for providing cells to a subject are adapted from a clinical protocol for cellular and adoptive immunotherapy that combines hematopoietic cell transplantation (HCT) and infusion of donor-derived NK cells into cancer patients. This clinical protocol was developed by Applicants and is currently offered at the Children's Hospital of Wisconsin and Froedtert Hospital in Milwaukee, Wis. In some cases, an adapted clinical protocol suitable for methods provided by the present invention comprises obtaining immune cells from a subject, genetically modifying the immune cells to express a chimeric antigen receptor having reduced cytokine production but substantially unaffected cytotoxicity relative to immune cells (i) having no genetic modification or (ii) expressing a CAR lacking a unique signaling molecule.

A further aspect of the present invention relates to immunomodulatory methods for reducing inflammatory ("toxic") cytokine production. For example, a method of reducing toxic cytokine production can comprise administration to a patient of an effective amount of polypeptide selected from at least three contiguous amino acids of the ADAP or Fyn polypeptides SEQ ID NO:1, 2, or 3. The polypeptide could be bound to other cargo delivery or stabilization elements known to one of skill in the art such as the HIV cell penetrating peptide Tat or to "stapled" peptides so that it could effectively be delivered to cells. One could also administer to a patient an effective amount of a small molecule which binds to either ADAP or Fyn at the position where ADAP and Fyn interact. The small molecule would interfere with the binding of ADAP and Fyn thereby disrupting the ability of Fyn to create signals to promote cytokine upregulation or release and the "toxic" effects.

In some cases, modified CAR-expressing NK cells and T cells are autologous to a subject and can be provided back to the subject. CAR-expressing cells are provided to a subject using an injection (e.g., intratumoral injection) or infusion (e.g., Intravenous infusion). A single injection or infusion may be required. In other cases, a treatment regimen comprises multiple injections or infusions of such modified immune cells.

A method according to the present invention can comprise obtaining NK cells or T cells from a subject. Examples of methods for obtaining immune cells from a subject or donor include harvesting cells by venipuncture, by apheresis methods, by white cell mobilization followed by apheresis or venipuncture, or by bone marrow aspiration. The preparation of cells after such procedures could include either positive or negative antibody selection techniques for cell surface markers specific to NK or T cells known by one of skill in the art.

Any appropriate method can be used to detect or measure inflammatory cytokine production and secretion. For example, cytokine or chemokine levels can be quantified using ELISA or multiplex assays. In some cases, cytokine or chemokine production can be assayed using intracellular staining. Other methods for detecting or measuring a cytokine level can include a Bioplex assay (Bio-Rad) for quantifying intracellular IFN-γ as well as methods described in detail in the Examples section.

In some cases, a chromium-release assay can be performed to determine the cytotoxicity of CAR-expressing NK cells or T cells. Chromium release assays determine the overall ability of cytotoxic T cells to lyse target cells expressing an epitope of interest by measuring released of radiolabeled chromium ($^{51}Cr$) from lysed target cells. In other cases, a flow cytometry-based cytotoxicity assay can be used to assess cytotoxicity in such cells. Other assays to determine cytotoxicity include granzyme assays (e.g., Granzyme B ELISpot), CD107a assays, enzyme-based assays, and Caspase-3 assays.

In some cases, a subject to which genetically modified cytotoxic cells are provided is monitored or assessed for increased (e.g., improved, more robust) tumor clearance. Accordingly, methods of the present invention are useful for cancer therapies. In exemplary embodiments, a method of the present invention is included in a cancer therapy in order to, for example, increase tumor clearance or clearance of cells expressing a particular antigen. For example, inclusion of the CD137 cytoplasmic tail in the signaling module of chimeric antigen receptors (CARs) in genetically-modified T or NK cells leads to efficient tumor clearance in patients. In some cases, a subject to which genetically modified cytotoxic cells are provided is monitored or assessed for clearance of cells expressing a particular antigen.

In another aspect, the present invention provides a method of screening a library of small molecules or drugs to identify compounds capable of reducing inflammatory cytokine release but without a concomitant loss of cytotoxicity. Therefore, a method of the present invention is to screen and identify molecules from a small molecule library that prevent toxic cytokine release or "cytokine release syndrome" without compromising the efficacy of tumor-specific cytotoxic molecules. Since loss of ADAP function does not compromise target cell (e.g., tumor cell) cytotoxicity, exemplary embodiments of the present invention provide a method for screening a pharmacological compound library to identify one or more molecules capable of binding to and inhibiting a function of ADAP, or one or more molecules capable of binding to and inhibiting a function of a molecule that binds to ADAP (e.g., FYN). Based on computational chemistry methods and in silico screening methods known in the art (see, e.g., Zhu et al., *Sci Transl Med.* 4(125): 125ra32 (2012); Sacchais et al., *Blood* 119(25):5955-62 (2012)), it is predicted that one or more molecules can be identified using a methods of the present invention, where the molecule has specificity for ADAP or Fyn and is capable of inhibiting downstream interactions of ADAP or Fyn with TAK1, Carma1, or the Carma1 signalosome.

Any appropriate screening method and/or method of analyzing biochemical interactions can be used in accordance with the present invention. For example, exemplary embodiments will include a fluorescent polarization assay to determine, for example, protein-protein interactions between a recombinant Fyn polypeptide or fragments thereof and a fluorescent ADAP polypeptide or fluorescent fragments thereof. Following optimization and adaptation of the fluorescent polarization assay in multi-well plates, a high-throughput screening method can be developed to identify test compounds that compete for binding and block interactions between Fyn or fragments thereof and fluorescent ADAP or fluorescent fragments thereof. A test compound can be added at any step of the assay protocol. If the test compound inhibits the binding between Fyn and fluorescent ADAP, a higher depolarization of fluorescence will be detected. Such a competitive binding assay can be reversed by incubating recombinant ADAP with fluorescent Fyn or fluorescent fragments thereof. In that case one would add a test compound to a tube or micro-well containing ADAP and fluorescent Fyn or fluorescent fragments thereof. A known compound could be any compound known to bind to ADAP in the region responsible for the interaction with Fyn, and most preferably a 3-60 amino acid polypeptide corresponding to region 600-657 of ADAP, or they could bind to fluorescent ADAP or fluorescent fragments thereof.

Another screening method useful according to a method described herein is an activated Natural Killer (NK) cell assay. Multiple measurements of inflammatory cytokine production can be used to determine the specificity of a test compound for NK cell activation. There are many means by which NK can be activated and a person having ordinary skill in the art would be able to use one of many methods. One such method uses an immobilized anti-NKG2D monoclonal antibody to activate NK cells in the presence or absence of the compounds. In some cases, an activated NK cell assay can be performed in a 384-well format in which the mitogenic antibody (anti-NKG2D monoclonal antibody) is immobilized in the well of a multi-well plate. Incubation of as low as 1000 NK cells per well and an overnight activation by the plate-bound anti-NKG2D antibody results in the production of inflammatory cytokines such as IFN-gamma. Culture supernatants from these 384-well plates can be assayed for one or more inflammatory cytokines using either a conventional enzyme-linked immunosorbant assay (ELISA) or a 384-well-based multiplex assay. Final results can be read using a conventional ELISA plate reader, an Infra-Red dye-based LI-COR Odyssey IR scanner, or another automated device or technique. Compounds can be screened in pools or as individual test samples. Selected compounds will be subjected to detailed laboratory analyses that will include in vitro (cytotoxicity and inflammatory cytokine production) and in vivo (tumor clearance or induced, experimental autoimmune disorders such as dextran sulfate-induced colitis and inflammatory cytokine production) in murine models.

In some cases, in vitro studies are performed to further analyze compounds identified according to a method of the present invention. For example, selected compounds can be analyzed using purified human primary NK cells using methodologies similar to those described above.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

Various exemplary embodiments of compositions and methods according to this invention are now described in the following non-limiting Examples. The Examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Mice and stable cell lines. C57BL/6 (wild-type) mice and Fyn$^{-/-}$ (B6; 129S7-Fyn$^{tm1sor}$/J, B6; 129SF2/J mice were from Jackson Laboratory. p110δ(D910A) (C57BL/6) mice have been described (Okkenhaug at al., *J. Immunol.* 177: 5122-5128 (2006)). Adap$^{-/-}$ mice were generated and backcrossed with C57BL/6 mice for at least six generations (Peterson et al., *Science* 293:2263-65 (2001)) and were also a gift from K. E. Nichols. Carma1(ΔCARD) (C57BL/6) mice and Carma1$^{-/-}$ (C57BL/6) mice have been described. See Newton et al., *Curr. Biol.* 13:1247-1251 (2003); Egawa et al., *Curr. Biol.* 13:1252-1258 (2003). Spleens from Map3k7$^{fl/fl}$Mx1-Cre mice (Tang et al., *J. Exp. Med.* 205: 1611-1619 (2008)) and Map3k7$^{fl/fl}$ mice (Sato et al., *Nat. Immunol.* 6:1087-1095 (2005)) were a gift from J. Zhang and Y. Xiao. All mice were maintained in pathogen-free conditions at the Biological Resource Center at the Medical College of Wisconsin and the Center for Immunology of the University of Minnesota. Female and male mice between the ages of 6 and 12 weeks were used. All animal protocols were approved by Institutional Animal Care and Use Committees and use of human PBMCs were approved by institutional review board committees. Map3k7$^{fl/fl}$ Mx1-Cre mice and Map3k7$^{fl/fl}$ mice were injected with poly(I:C) (5 μg per gram body weight) on day 1 and day 3 to induce knockdown of Map3k7. Spleens of treated mice were collected on day 4 (Tang et al., *J. Exp. Med.* 205:1611-1619 (2008)). EL4 and K562 cells (American Type Culture Collection) were maintained in RPMI-1640 medium containing 10% heat-inactivated FBS (Life Technologies). Those cell lines were periodically tested to exclude the possibility of mycoplasma contamination. The generation of stable H60-expressing EL4 cell lines has been described. See Regunathan et al., *Blood* 105:233-240 (2005). For the generation of stable CD137L-expressing EL4 cell lines, full-length mouse cDNA encoding CD137L was amplified with primers CD137L-F (5' CGCGGATCCATGGACCAGCACACACT-TGAT G 3') and CD137L-R (5' CTAGTCTA-GAAAAACATAGCAGCTTGAGG 3'). That cDNA was cloned into pCDNA3 between BamHI and XbaI sites and was used to transfect EL4 cells by electroporation (300 volts, 25 μF) (GenePulser, BioRad). Transfected cells were maintained in RPMI-1640 medium with 10% FBS. After 12 hours, fresh medium containing 10 mg/ml G418 (Cellgro) was added and stable cell clones were analyzed for CD137L expression by flow cytometry and PCR. CD137L$^+$ clones were maintained in 1 mg/ml aminoglycoside G418.

Antibodies. Anti-NK1.1 (PK136), anti-CD3ε (17A2 or 145-2C11), anti-NKG2D (A10), anti-CD137 (17b5), anti-CD137L (TKS-1), anti-human IFN-γ (MG1.2) and anti-human CD107a (1D4B) were from e-Bioscience. Anti-Ly49D (4E5) was from BD Pharmingen. Anti-H60a, antibody to total Jnk1-Jnk2 (MAB2076) and anti-NCR1 (MA82225) were from R&D Systems. Anti-TAK1 (07-263) and anti-β-actin (C4) were from Millipore. Antibody to TAK1 phosphorylated at Thr184 and Thr187 (90C7), antibody to Jnk1-Jnk2 phosphorylated at Thr183 and Tyr185 (98-F2), anti-Erk1-Erk2 (137F5), antibody to Erk1-Erk2 phosphorylated at Thr202 and Tyr204 (D13.14.4E), anti-p38 (9212), antibody to p38 phosphorylated at Thr180 and Tyr182 (3D7), anti-PKC-θ (2059), antibody to PKC-θ phosphorylated at Thr538 (9377), anti-PLC-γ2 (3872), antibody to PLC-γ2 phosphorylated at Tyr1217 (3871), antibody to PI(3)K subunits p85α and p55α phosphorylated at Tyr458 and Tyr199 (4228), anti-IκBα (L35A5), antibody to IκBα phosphorylated at Ser32 (14D4), antibody to NF-κB subunit p65 (D14E12), anti-c-Fos (9F6), anti-c-Jun (60A8) and anti-Carma1 (1D12) were from Cell Signaling Technologies. Anti-ADAP (07-546) and anti-p85α (06-497) were from Upstate. Antibody to Akt phosphorylated at Thr308 (sc-16646-R), anti-Akt (c20; sc-1618), anti-YY1 (H-10; sc-7341), anti-Fyn (FYN3; sc-16-G), anti-Lck (3A5; sc-433) and anti-Carma1 (sc-20458) were from Santa Cruz Biotechnology. Antibody to Fyn phosphorylated at Tyr530 (ab53690) was from Abcam. Anti-Fyn (Fyn-59), anti-CD45.1 (A20) and anti-CD45.2 (104) were from BioLegend. Antibody to the C terminus of Carma1 (NB100-1200) was from Novus Biologicals.

NK cell preparation. NK cells were purified as described (Liu et al., *Proc. Natl. Acad. Sci. U.S.A.* 95:8779-8784 (1998)). Single-cell suspensions from spleen were passed through nylon wool columns for depletion of adherent populations consisting of B cells and macrophages. Cells that did not adhere to nylon wool were cultured with 1,000 U/ml of IL-2 (NCI-BRB-Preclinical Repository). The purity of the NK cultures was checked, and preparations with more than 95% of NK1.1$^+$ cells were used on day 7.

Transfection. NK cells were transfected with specific siRNA or scrambled siRNA (NC1; IDT DNA Technologies) with Amaxa mouse T cell Nucleofector medium (VZB-1001; Lonza) and an Amaxa 96-well shuttle Nucleofector (Lonza). Human NK cells were transfected by nucleofection with an Amaxa human NK Nucleofector kit (VPA-1005; Lonza). NK cells ($3 \times 10^6$) cultured in IL-2 were resuspended in 90 μl of Nucleofector solution and transfected by electroporation with a final siRNA concentration of 0.02 μM with an Amaxa Nucleofector (Lonza). Mouse NK cells were treated with siRNA specific for Lck (5' GGUUCUU-CAAGAAUCUGAGCCGUAA 3'; 3' AAC-CAAGAAGUUCUUAGACUC GGCAUU 5'; N001162432.12.3; Integrated DNA Technologies) or Lat (5' AGAAUCU ACAGGAGCUUAACUGAAA 3'; 3' ACUC-UUAGAUGUCCUCGAAUUGACUUU 5'; N010689.12.1; Integrated DNA Technologies). Human NK cells were treated with ADAP-specific siRNA (5' UGGCUA-CAAUUAUGAAGAAGUUGAA 3'; 3' AAACCG AUGUUAAUACUUCUUCAACUU 5'; N001465.12.1; Integrated DNA Technologies) or scrambled siRNA (NC1), cultured for 16 hours in 10% RPMI medium supplemented with 1,000 U/ml IL-2 (NCI-BRB-Preclinical Repository) and used for functional studies.

Flow cytometry. NK cells cultured in IL-2, stable cell lines or single-cell preparations from spleen or lungs were stained with fluorescence-labeled mAbs in 1% FCS-PBS as described. See Regunathan et al., *Blood* 105:233-240 (2005). Phycoerythrin-conjugated anti-mouse CD137L (TKS-1), eFluor 450-conjugated anti-mouse CD3ε (17A2), allophycocyanin-conjugated anti-NK1.1 (PK136), phycoerythrin-indotricarbocyanine-conjugated anti-IFN-γ (XMG1.2), phycoerythrin-conjugated anti-mouse CD107a (ebio1D4B), phycoerythrin-conjugated anti-mouse NKG2D (A10) and phycoerythrin-conjugated anti-mouse CD137 (17B5) were from eBioscience. Alexa Fluor 488-conjugated anti-mouse CD45.1 (A20) and Pacific blue-conjugated anti-mouse CD45.2 (104) were from BioLegend. Phycoerythrin-conjugated anti-mouse H60 (205326) was from R&D Systems. An LSR II was used for standard flow cytometry ($3 \times 10^6$ events analyzed per sample) and data were analyzed with FACSDiva software (BD) or FlowJo software (TreeStar).

Cytotoxicity assays. NK cell-mediated cytotoxicity against EL4 cells, EL4 cells stably expressing H60 or CD137L and K562 cells was quantified by $^{51}$Cr-release assays at varied rations of effector cells to target cells (Mason at al., *J. Exp. Med.*, 184:2119-28 (1996)). Specific lysis was calculated by the amount of absolute, spontaneous and experimental release of $^{51}$Cr from target cells.

Co-culture assays. NK cells ($1 \times 10^5$) that had been cultured in IL-2 were cultured with equal numbers of EL4 cells, EL4-CD137L$^{hi}$ or EL4-H60$^{hi}$ cell lines and were cultured for 18 hours in RPMI-1640 medium supplemented with 10% FBS. Cytokines and chemokines were measured in culture supernatants by Bioplex assay.

Quantification of cytokines and chemokines. NK cells were cultured in IL-2, then Fc receptors were blocked with mAb to CD16-CD32 (2.4G2; BD Pharmingen) and cells were activated for 18 hours with plate-bound mitogenic anti-CD137 (17B5; eBioscience), anti-NKG2D (A10; eBioscience) or Ly49D (4E5; BD Pharmingen). Culture supernatants were analyzed by Bioplex assay (Bio-Rad). Intracellular IFN-γ was quantified as described (Malarkannan et al., *Immunity* 13:333-344 (2000)). NK cells in which Fc receptors had been blocked were activated with plate-bound mAbs (identified above) in the presence of brefeldin A. After 12 hours, cells were stained for surface CD3ε and NK1.1 (antibodies identified above), fixed, permeabilized and stained with phycoerythrin-indotricarbocyanine-conjugated mAb to IFN-γ (XMG1.2; eBioscience). For inhibition assays, NK cells were incubated for 1 hour with varying concentrations of C8863 (Lck inhibitor), U73122 (PLC-γ inhibitor) and rottlerin (PKC inhibitor), then were washed and added to plates coated with mAb to NKG2D or mAb to CD137 (identified above). After 18 hours, IFN-γ was quantified in the culture supernatants by enzyme-linked immunosorbent assay. Where necessary, NK cells that had been cultured in IL-2 were treated with IL-12 (1 ng/mL; R&D Systems) and IL-18 (10 n/mL; MBL), and the supernatants were analyzed similarly. For quantification of Ifng mRNA, NK cells were activated for 6 hours and lysed, and total RNA was purified with an RNeasy Mini Kit (Qiagen). Real-time PCR was done with a SYBR green protocol and an ABI7900 HT thermal cycler. Transcripts in each sample were assayed in triplicate, and the mean cycling threshold was used for calculation of the change in expression. The control (housekeeping) gene Gapdh was used for global normalization in each experiment. Primer sequences for Ifng were 5' GACTGTGATTGCGGGGTTGT 3' (sense) and 5' GGCCCGGAGTGTAGACATCT 3' (anti-sense).

Immunoprecipitation. Unstimulated NK cells or NK cells activated with plate-bound antibody (identified above) were lysed with immunoprecipitation lysis buffer containing Tris (pH 7.5, 20 mM), NaCl (150 mM), EDTA (1 mM), EGTA (1 mM), Triton-X100 (1%), sodium pyrophosphate (2.5 mM), β-glycerophosphate (1 mM), sodium orthovanadate (1 mM), leupeptin (1 ug/ml) and PMSF (1 mM). Lysates were centrifuged for removal of debris, For immunoprecipitation, 300-500 μg of each lysate was incubated for 1 hour at 4° C. with 2 μg of the appropriate antibody (identified above). 20 μl of Protein G PLUS-Agarose (Santa Cruz Biotechnology) was added, followed by incubation overnight at 4° C. After centrifugation, the supernatant was aspirated and beads were washed with the immunoprecipitation lysis buffer. SDS sample buffer (6×, reducing; BP-111R; Boston BioProducts), diluted to 1× concentration with the immunoprecipitation lysis buffer, was added to the bead pellet, followed by denaturation for 10 min at 95° C. Samples were separated by 10% SDS-PAGE.

Immunoblot analysis. Whole-cell lysates (15-20 μg) or nuclear protein extracts (10 μg) isolated with NE-PER reagent (Pierce) were resolved by 10% SDS-PAGE, transferred to PVDF membranes and probed with the appropriate antibodies (identified above). Signals were detected with the SuperSignal West Pico Chemiluminescent Substrate (Thermo Scientific). Band intensities of phosphorylated proteins were normalized to those of the respective total protein. The change in phosphorylation after 5, 20, or 60 minutes of activation was calculated with those normalized values. For immunoprecipitation experiments, the induction of the protein after activation was calculated based on the basal amount of that protein in the unstimulated condition, after normalization to the protein immunoprecipitated, with ImageJ software.

Adoptive transfer. Bone marrow cells were isolated from CD45.1$^+$ B6.SJL mice (4007; Taconic), CD45.2$^+$ Adap$^{-/-}$ mice and CD45.2$^+$ Carma1$^{-/-}$ mice. B10; B6-Rag2$^{tm1Fwa}$// 2rg$^{tm1Wjl}$ mice deficient in recombination-activating gene 2 and the common γ-chain (4111; Taconic) were used as recipients. Bone marrow cells from CD45.1$^+$ wild-type and CD45.2$^+$ mice were mixed (1×10$^6$ per genotype) and were injected retro-orbitally into the sublethally irradiated (800 cGy) recipient mice. After 4 weeks, spleen samples from the reconstituted mice were enriched for NK cells through the use of nylon wool as described (Regunathan et al., *J. Immunol.* 177:5365-5376 (2006)) and were cultured overnight or for 7 days with 1,000 U/ml IL-2. Those NK cells were activated with plate-bound mAb to NKG2D, mAb to CD137 or mAb to Ly49D (identified above) and were analyzed by flow cytometry for surface expression of CD107a or for intracellular IFN-γ (antibodies identified above). The donor origin of NK cells were determined by cell surface expression of CD45.1 or CD45.2. The frequency of CD107a$^+$ and IFN-γ$^+$ NK cells among CD45.1$^+$ wild-type and CD45.2$^+$ mutant NK cells after activation mediated by plate-bound antibody were compared.

Isolation, activation and functional analysis of human NK cells. PBMCs were isolated from 25-30 mL of human buffy coats obtained from donors, all of whom had provided informed consent to the BloodCenter of Wisconsin, with Ficoll-Plaque Plus (17-1440-02; GE Healthcare). All samples were identified only by their unique patient number. NK cells were negatively selected from PBMCs with an EasySep Human NK Cell Enrichment Kit (19055; StemCell Technologies). Human NK cells were activated with plate-bound anti-NKG2D (1D11; eBioscience) or anti-CD137 (4B4-1; BioLegend). For analysis of the degranulation of NK cells, 1×10$^5$ NK cells were activated for 4 hours with plate-bound anti-NKG2D or anti-CD137 in 10% RPMI medium containing phycoerythrin-conjugated antibody to human CD107a (H4A3; BioLegend). NK cells were stained with mAb to human CD56 (301040; R&D Systems). Residual T cells were gated out with Alexa Fluor 700-conjugated mAb to human CD3 (UCHT1; eBioscience). For the analysis of cytokine production, 1×10$^5$ human NK cells were activated for 18 hours with plate-bound mAb to NKG2D or mAb to CD137 in 200 μL 10% RPMI medium. Cytokines and chemokines were measured with a Multiplex kit (BioRad).

Experimental data and statistical analysis. Total sample numbers were determined on the basis of previous studies (from our laboratories and other laboratories) with similar transgenic mouse models with comparable functional defects. Randomization method or 'blinding' of investigators to group allocation was not used. A paired, two-sample Student's t-test was used for statistical analysis, with equal or unequal variance, depending on the type of data. P values of 0.05 or less were considered significant. Normal distribution of sample variance was assumed on the basis of earlier studies from other laboratories with data sets similar to ours.

TABLE 1

Interacting Motifs in ADAP Amino Acid Sequence for Signaling Partners

| Signaling Partner | Decoy Peptide from Mouse ADAP (residues of SEQ ID NO: 3) | Decoy Peptide from Human ADAP (residues of SEQ ID NO: 1) |
|---|---|---|
| Fyn | PTDDEIYDGIEE (609-620) | PPDDDIYDGIEE (619-630) |
| Carma1 | EEQESEGETYEDIDSS KERD (441-460) IHHAKACCDVKGGKNE LSFK (501-520) | EEQDSEGETYEDIEASKE RE (453-472) IHLAKACCDVKGGKNELS FK (513-532) |
| TAK1 | DASDFPPPPAEMSQGM SV (691-708) | DTSDFPVSSAEMSQGTNV (655-672) |
| SLP76 | DQDVYDDVAE (580-589) GEEVYDDVDA (683-692) | DQEVYDDVAE (591-600) GDEVYDDVDT (647-656) |
| SKAP55 | PPVPSIPPRNIK (402-413) | PPVPSLPPRNIK (414-425) |

I claim:

1. A method of decreasing or preventing cytokine release syndrome (CRS) by disrupting release of at least one cytokine selected from the group consisting of IFNγ, GM-CSF, MIP-1α, MIP-1β, and RANTES in a subject receiving chimeric antigen receptor cytotoxic cell therapy, the method comprising
   genetically modifying a CD8+ T lymphocyte or NK cytotoxic cell to express (a) an inhibitor of ADAP-Fyn binding and (b) a chimeric antigen receptor comprising an extracellular domain and a signaling moiety selected from the group consisting of the CD137 cytoplasmic domain and the NKG2D cytoplasmic domain, wherein the cytotoxicity of the genetically modified CD8+ T lymphocyte or NK cytotoxic cell is substantially unchanged relative to the CD8+ T lymphocyte or NK cytotoxic cell not expressing the inhibitor of ADAP-Fyn binding; and
   providing to the subject the genetically modified CD8+ T lymphocyte or NK cytotoxic cell;
   wherein expression of the inhibitor of ADAP-Fyn binding in the genetically modified CD8+ T lymphocyte or natural Killer (NK) cytotoxic cell disrupts release of the at least one cytokine selected from the group consisting of IFN-γ, GM-CSF, MIP-1α, MIP-1β, and RANTES and decreases or prevents CRS in the subject.

2. The method of claim 1, wherein the cytotoxic cell is autologous to the subject.

3. The method of claim 1, wherein the cytotoxic cell is derived from bone marrow of the subject.

4. The method of claim 1, wherein the cytotoxic cell is derived from a stem cell.

5. The method of claim 4, wherein the stem cell is a human pluripotent stem cell.

6. The method of claim 5, wherein the human pluripotent stem cell is an induced pluripotent stem cell obtained from a somatic cell of the subject.

7. The method of claim 1, wherein the chimeric antigen receptor has specificity for a subset of immune cells.

8. The method of claim 1, wherein the chimeric antigen receptor has specificity for a tumor antigen.

9. The method of claim 1, wherein the chimeric antigen receptor has specificity for a viral antigen.

10. The method of claim 1, wherein the chimeric antigen receptor has specificity for a bacterial antigen.

11. The method of claim 1, wherein the inhibitor is a decoy polypeptide.

12. The method of claim 11, wherein the decoy polypeptide is expressed using a vector comprising an internal ribosome entry site (IRES) sequence.

13. The method of claim 1, wherein the inhibitor comprises at least an ADAP polypeptide portion comprising at least 3 contiguous amino acids selected from the residues 600-630 of SEQ ID NO: 1.

14. The method of claim 1, wherein the inhibitor comprises at least an ADAP polypeptide portion comprising at least 3 contiguous amino acids selected from the residues 619-630 of SEQ ID NO: 1.

15. The method of claim 1, wherein the inhibitor comprises at least an ADAP polypeptide portion comprising at least 3 contiguous amino acids selected from the residues 600-640 of SEQ ID NO: 1.

16. The method of claim 1, wherein the inhibitor comprises at least an ADAP polypeptide portion comprising at least 3 contiguous amino acids selected from the residues 609-620 of SEQ ID NO: 3.

17. The method of claim 13, wherein the at least 3 amino acids comprise at least one conservative amino acid substitution or non-conservative amino acid substitution, whereby the inhibitor has increased stability or longer half-life relative to an inhibitor lacking the at least one amino acid substitution.

18. The method of claim 1, wherein the extracellular domain of the chimeric antigen receptor specifically binds to a CD cell surface protein.

19. The method of claim 1, wherein the extracellular domain of the chimeric antigen receptor specifically binds to the CD19, CD20, CD22, ROR1, or GD2 antigen.

20. A method of decreasing or preventing cytokine release syndrome (CRS) by disrupting release of at least one cytokine selected from the group consisting of IFNγ, GM-CSF, MIP-1α, MIP-1β, and RANTES in a subject receiving chimeric antigen receptor cytotoxic cell therapy, the method comprising
   genetically modifying a CD8+ T lymphocyte or NK cytotoxic cell to express (a) a decoy peptide inhibitor of ADAP-Fyn binding comprising at least an ADAP polypeptide portion comprising at least 3 contiguous amino acids selected from the residues 600-640 of SEQ ID NO: 1 and (b) a chimeric antigen receptor comprising an extracellular domain and a signaling moiety selected from the group consisting of the CD137 cytoplasmic domain and the NKG2D cytoplasmic domain, wherein the cytotoxicity of the genetically modified CD8+ T lymphocyte or NK cytotoxic cell is substantially unchanged relative to the CD8+ T lymphocyte or NK cytotoxic cell not expressing the inhibitor of ADAP-Fyn binding; and
   providing to the subject the genetically modified CD8+ T lymphocyte or NK cytotoxic cell;

wherein expression of the decoy peptide inhibitor of ADAP-Fyn binding in the genetically modified CD8+ T lymphocyte or natural Killer (NK) cytotoxic cell disrupts release of the at least one cytokine selected from the group consisting of IFN-γ, GM-CSF, MIP-1α, MIP-1β, and RANTES and decreases or prevents CRS in the subject.

21. The method of claim 20, wherein the at least 3 contiguous amino acids are selected from residues 600-630 of SEQ ID NO:1.

22. The method of claim 21, wherein the at least 3 contiguous amino acids selected from residues 619-630 of SEQ ID NO:1.

23. The method of claim 20, wherein the at least 3 amino acids comprise at least one conservative amino acid substitution or non-conservative amino acid substitution, whereby the inhibitor has increased stability or longer half-life relative to an inhibitor lacking the at least one amino acid substitution.

24. The method of claim 20, wherein the cytotoxic cell is autologous to the subject.

25. The method of claim 20, wherein the cytotoxic cell is derived from bone marrow of the subject.

26. The method of claim 20, wherein the cytotoxic cell is derived from a stem cell.

27. The method of claim 26, wherein the stem cell is a human pluripotent stem cell.

28. The method of claim 27, wherein the human pluripotent stem cell is an induced pluripotent stem cell obtained from a somatic cell of the subject.

29. The method of claim 20, wherein the chimeric antigen receptor has specificity for a subset of immune cells.

30. The method of claim 20, wherein the chimeric antigen receptor has specificity for a tumor antigen.

31. The method of claim 20, wherein the chimeric antigen receptor has specificity for a viral antigen.

32. The method of claim 20, wherein the chimeric antigen receptor has specificity for a bacterial antigen.

33. The method of claim 20, wherein the decoy polypeptide inhibitor is expressed using a vector comprising an internal ribosome entry site (IRES) sequence.

34. The method of claim 20, wherein the extracellular domain of the chimeric antigen receptor specifically binds to a CD cell surface protein.

35. The method of claim 20, wherein the extracellular domain of the chimeric antigen receptor specifically binds to the CD19, CD20, CD22, ROR1, or GD2 antigen.

36. The method of claim 1, wherein the signaling moiety is the CD137 cytoplasmic domain.

37. The method of claim 20, wherein the signaling moiety is the CD137 cytoplasmic domain.

\* \* \* \* \*

UNITED STATES PATENT AND TRADEMARK OFFICE
CERTIFICATE OF CORRECTION

PATENT NO. : 10,786,532 B2  
APPLICATION NO. : 14/433082  
DATED : September 29, 2020  
INVENTOR(S) : Malarkannan Page 1 of 1

It is certified that error appears in the above-identified patent and that said Letters Patent is hereby corrected as shown below:

In the Specification

Column 5, Line 14, "of FN-γ" should be --of IFN-γ--.

Column 5, Line 20, "NE-κB" should be --NF-κB--.

Column 16, Line 6, "at al.," should be --et al.,--.

Column 16, Line 55, "MA82225" should be --MAB2225--.

Column 18, Line 2, "at al.," should be --et al.,--.

Column 18, Line 34, "10 n/mL" should be --10 ng/mL--.

Signed and Sealed this  
Second Day of February, 2021

Drew Hirshfeld  
*Performing the Functions and Duties of the  
Under Secretary of Commerce for Intellectual Property and  
Director of the United States Patent and Trademark Office*

SEQUENCE LISTING

<160> NUMBER OF SEQ ID NOS: 3

<210> SEQ ID NO 1
<211> LENGTH: 783
<212> TYPE: PRT
<213> ORGANISM: Homo sapiens

<400> SEQUENCE: 1

Met Ala Lys Tyr Asn Thr Gly Gly Asn Pro Thr Glu Asp Val Ser Val
1               5                   10                  15

Asn Ser Arg Pro Phe Arg Val Thr Gly Pro Asn Ser Ser Ser Gly Ile
                20                  25                  30

Gln Ala Arg Lys Asn Leu Phe Asn Asn Gln Gly Asn Ala Ser Pro Pro
            35                  40                  45

```
Ala Gly Pro Ser Asn Val Pro Lys Phe Gly Ser Pro Lys Pro Val
    50                  55                  60
Ala Val Lys Pro Ser Ser Glu Glu Lys Pro Asp Lys Glu Pro Lys Pro
65                  70                  75                  80
Pro Phe Leu Lys Pro Thr Gly Ala Gly Gln Arg Phe Gly Thr Pro Ala
                85                  90                  95
Ser Leu Thr Thr Arg Asp Pro Glu Ala Lys Val Gly Phe Leu Lys Pro
            100                 105                 110
Val Gly Pro Lys Pro Ile Asn Leu Pro Lys Glu Asp Ser Lys Pro Thr
        115                 120                 125
Phe Pro Trp Pro Pro Gly Asn Lys Pro Ser Leu His Ser Val Asn Gln
    130                 135                 140
Asp His Asp Leu Lys Pro Leu Gly Pro Lys Ser Gly Pro Thr Pro Pro
145                 150                 155                 160
Thr Ser Glu Asn Glu Gln Lys Gln Ala Phe Pro Lys Leu Thr Gly Val
                165                 170                 175
Lys Gly Lys Phe Met Ser Ala Ser Gln Asp Leu Glu Pro Lys Pro Leu
            180                 185                 190
Phe Pro Lys Pro Ala Phe Gly Gln Lys Pro Pro Leu Ser Thr Glu Asn
        195                 200                 205
Ser His Glu Asp Glu Ser Pro Met Lys Asn Val Ser Ser Lys Gly
    210                 215                 220
Ser Pro Ala Pro Leu Gly Val Arg Ser Lys Ser Gly Pro Leu Lys Pro
225                 230                 235                 240
Ala Arg Glu Asp Ser Glu Asn Lys Asp His Ala Gly Glu Ile Ser Ser
                245                 250                 255
Leu Pro Phe Pro Gly Val Val Leu Lys Pro Ala Ala Ser Arg Gly Gly
            260                 265                 270
Pro Gly Leu Ser Lys Asn Gly Glu Glu Lys Glu Asp Arg Lys Ile
        275                 280                 285
Asp Ala Ala Lys Asn Thr Phe Gln Ser Lys Ile Asn Gln Glu Glu Leu
        290                 295                 300
Ala Ser Gly Thr Pro Pro Ala Arg Phe Pro Lys Ala Pro Ser Lys Leu
305                 310                 315                 320
Thr Val Gly Gly Pro Trp Gly Gln Ser Gln Glu Lys Glu Lys Gly Asp
                325                 330                 335
Lys Asn Ser Ala Thr Pro Lys Gln Lys Pro Leu Pro Pro Leu Phe Thr
            340                 345                 350
Leu Gly Pro Pro Pro Lys Pro Asn Arg Pro Pro Asn Val Asp Leu
        355                 360                 365
Thr Lys Phe His Lys Thr Ser Ser Gly Asn Ser Thr Ser Lys Gly Gln
        370                 375                 380
Thr Ser Tyr Ser Thr Thr Ser Leu Pro Pro Pro Pro Ser His Pro
385                 390                 395                 400
Ala Ser Gln Pro Pro Leu Pro Ala Ser His Pro Ser Gln Pro Pro Val
                405                 410                 415
Pro Ser Leu Pro Pro Arg Asn Ile Lys Pro Pro Phe Asp Leu Lys Ser
            420                 425                 430
Pro Val Asn Glu Asp Asn Gln Asp Gly Val Thr His Ser Asp Gly Ala
        435                 440                 445
Gly Asn Leu Asp Glu Gln Asp Ser Glu Gly Glu Thr Tyr Glu Asp
    450                 455                 460
Ile Glu Ala Ser Lys Glu Arg Glu Lys Lys Arg Glu Lys Glu Glu Lys
```

```
                465                 470                 475                 480
Lys Arg Leu Glu Leu Glu Lys Lys Gln Lys Glu Lys Glu Lys Lys
                    485                 490                 495
Glu Gln Glu Ile Lys Lys Phe Lys Leu Thr Gly Pro Ile Gln Val
                500                 505                 510
Ile His Leu Ala Lys Ala Cys Cys Asp Val Lys Gly Lys Asn Glu
                515                 520                 525
Leu Ser Phe Lys Gln Gly Glu Gln Ile Glu Ile Arg Ile Thr Asp
                530                 535                 540
Asn Pro Glu Gly Lys Trp Leu Gly Arg Thr Ala Arg Gly Ser Tyr Gly
545                 550                 555                 560
Tyr Ile Lys Thr Thr Ala Val Glu Ile Asp Tyr Asp Ser Leu Lys Leu
                    565                 570                 575
Lys Lys Asp Ser Leu Gly Ala Pro Ser Arg Pro Ile Glu Asp Asp Gln
                580                 585                 590
Glu Val Tyr Asp Asp Val Ala Glu Gln Asp Asp Ile Ser Ser His Ser
                595                 600                 605
Gln Ser Gly Ser Gly Gly Ile Phe Pro Pro Pro Asp Asp Asp Ile
                610                 615                 620
Tyr Asp Gly Ile Glu Glu Asp Ala Asp Asp Gly Phe Pro Ala Pro
625                 630                 635                 640
Pro Lys Gln Leu Asp Met Gly Asp Glu Val Tyr Asp Asp Val Asp Thr
                    645                 650                 655
Ser Asp Phe Pro Val Ser Ser Ala Glu Met Ser Gln Gly Thr Asn Val
                    660                 665                 670
Gly Lys Ala Lys Thr Glu Glu Lys Asp Leu Lys Lys Leu Lys Gln
                675                 680                 685
Glu Lys Glu Glu Lys Asp Phe Arg Lys Lys Phe Lys Tyr Asp Gly Glu
                    690                 695                 700
Ile Arg Val Leu Tyr Ser Thr Lys Val Thr Thr Ser Ile Thr Ser Lys
705                 710                 715                 720
Lys Trp Gly Thr Arg Asp Leu Gln Val Lys Pro Gly Glu Ser Leu Glu
                    725                 730                 735
Val Ile Gln Thr Thr Asp Asp Thr Lys Val Leu Cys Arg Asn Glu Glu
                    740                 745                 750
Gly Lys Tyr Gly Tyr Val Leu Arg Ser Tyr Leu Ala Asp Asn Asp Gly
                755                 760                 765
Glu Ile Tyr Asp Asp Ile Ala Asp Gly Cys Ile Tyr Asp Asn Asp
                770                 775                 780

<210> SEQ ID NO 2
<211> LENGTH: 537
<212> TYPE: PRT
<213> ORGANISM: Homo sapiens

<400> SEQUENCE: 2

Met Gly Cys Val Gln Cys Lys Asp Lys Glu Ala Thr Lys Leu Thr Glu
1               5                   10                  15

Glu Arg Asp Gly Ser Leu Asn Gln Ser Ser Gly Tyr Arg Tyr Gly Thr
                20                  25                  30

Asp Pro Thr Pro Gln His Tyr Pro Ser Phe Gly Val Thr Ser Ile Pro
                35                  40                  45

Asn Tyr Asn Asn Phe His Ala Ala Gly Gly Gln Gly Leu Thr Val Phe
                50                  55                  60
```

```
Gly Gly Val Asn Ser Ser Ser His Thr Gly Thr Leu Arg Thr Arg Gly
 65                  70                  75                  80
Gly Thr Gly Val Thr Leu Phe Val Ala Leu Tyr Asp Tyr Glu Ala Arg
                 85                  90                  95
Thr Glu Asp Asp Leu Ser Phe His Lys Gly Glu Lys Phe Gln Ile Leu
            100                 105                 110
Asn Ser Ser Glu Gly Asp Trp Trp Glu Ala Arg Ser Leu Thr Thr Gly
        115                 120                 125
Glu Thr Gly Tyr Ile Pro Ser Asn Tyr Val Ala Pro Val Asp Ser Ile
    130                 135                 140
Gln Ala Glu Glu Trp Tyr Phe Gly Lys Leu Gly Arg Lys Asp Ala Glu
145                 150                 155                 160
Arg Gln Leu Leu Ser Phe Gly Asn Pro Arg Gly Thr Phe Leu Ile Arg
                165                 170                 175
Glu Ser Glu Thr Thr Lys Gly Ala Tyr Ser Leu Ser Ile Arg Asp Trp
            180                 185                 190
Asp Asp Met Lys Gly Asp His Val Lys His Tyr Lys Ile Arg Lys Leu
        195                 200                 205
Asp Asn Gly Gly Tyr Tyr Ile Thr Thr Arg Ala Gln Phe Glu Thr Leu
    210                 215                 220
Gln Gln Leu Val Gln His Tyr Ser Glu Arg Ala Ala Gly Leu Cys Cys
225                 230                 235                 240
Arg Leu Val Val Pro Cys His Lys Gly Met Pro Arg Leu Thr Asp Leu
                245                 250                 255
Ser Val Lys Thr Lys Asp Val Trp Glu Ile Pro Arg Glu Ser Leu Gln
            260                 265                 270
Leu Ile Lys Arg Leu Gly Asn Gly Gln Phe Gly Glu Val Trp Met Gly
        275                 280                 285
Thr Trp Asn Gly Asn Thr Lys Val Ala Ile Lys Thr Leu Lys Pro Gly
    290                 295                 300
Thr Met Ser Pro Glu Ser Phe Leu Glu Glu Ala Gln Ile Met Lys Lys
305                 310                 315                 320
Leu Lys His Asp Lys Leu Val Gln Leu Tyr Ala Val Val Ser Glu Glu
                325                 330                 335
Pro Ile Tyr Ile Val Thr Glu Tyr Met Asn Lys Gly Ser Leu Leu Asp
            340                 345                 350
Phe Leu Lys Asp Gly Glu Gly Arg Ala Leu Lys Leu Pro Asn Leu Val
        355                 360                 365
Asp Met Ala Ala Gln Val Ala Ala Gly Met Ala Tyr Ile Glu Arg Met
    370                 375                 380
Asn Tyr Ile His Arg Asp Leu Arg Ser Ala Asn Ile Leu Val Gly Asn
385                 390                 395                 400
Gly Leu Ile Cys Lys Ile Ala Asp Phe Gly Leu Ala Arg Leu Ile Glu
                405                 410                 415
Asp Asn Glu Tyr Thr Ala Arg Gln Gly Ala Lys Phe Pro Ile Lys Trp
            420                 425                 430
Thr Ala Pro Glu Ala Ala Leu Tyr Gly Arg Phe Thr Ile Lys Ser Asp
        435                 440                 445
Val Trp Ser Phe Gly Ile Leu Leu Thr Glu Leu Val Thr Lys Gly Arg
    450                 455                 460
Val Pro Tyr Pro Gly Met Asn Asn Arg Glu Val Leu Glu Gln Val Glu
465                 470                 475                 480
Arg Gly Tyr Arg Met Pro Cys Pro Gln Asp Cys Pro Ile Ser Leu His
```

```
                    485                 490                 495
Glu Leu Met Ile His Cys Trp Lys Lys Asp Pro Glu Glu Arg Pro Thr
                    500                 505                 510

Phe Glu Tyr Leu Gln Ser Phe Leu Glu Asp Tyr Phe Thr Ala Thr Glu
                    515                 520                 525

Pro Gln Tyr Gln Pro Gly Glu Asn Leu
                    530                 535

<210> SEQ ID NO 3
<211> LENGTH: 819
<212> TYPE: PRT
<213> ORGANISM: Mus musculus

<400> SEQUENCE: 3

Met Ala Lys Phe Asn Thr Gly Ser Asn Pro Thr Glu Glu Ala Ala Thr
1               5                   10                  15

Ser Ser Arg Pro Phe Lys Val Ala Gly Gln Ser Ser Pro Ser Gly Ile
                20                  25                  30

Gln Ser Arg Lys Asn Leu Phe Asp Asn Gln Gly Asn Ala Ser Pro Pro
            35                  40                  45

Ala Gly Pro Ser Ser Met Pro Lys Phe Gly Thr Thr Lys Pro Pro Leu
        50                  55                  60

Ala Ala Lys Pro Thr Tyr Glu Glu Lys Pro Glu Lys Glu Pro Lys Pro
65                  70                  75                  80

Pro Phe Leu Lys Pro Thr Gly Gly Ser Pro Arg Phe Gly Thr Gln Pro
                85                  90                  95

Asn Ser Val Ser Arg Asp Pro Glu Val Lys Val Gly Phe Leu Lys Pro
                100                 105                 110

Val Ser Pro Lys Pro Thr Ser Leu Thr Lys Glu Asp Ser Lys Pro Val
            115                 120                 125

Val Leu Arg Pro Pro Gly Asn Lys Leu His Asn Leu Asn Gln Glu Ser
        130                 135                 140

Asp Leu Lys Thr Pro Gly Pro Lys Pro Gly Pro Ala Pro Pro Val Pro
145                 150                 155                 160

Glu Asn Glu Leu Lys Pro Gly Phe Ser Lys Val Ala Gly Ala Lys Ser
                165                 170                 175

Lys Phe Met Pro Ala Ala Gln Asp Thr Asp Ser Lys Pro Arg Phe Pro
                180                 185                 190

Arg His Thr Phe Gly Gln Lys Pro Ser Leu Ser Thr Glu Asp Ser Gln
            195                 200                 205

Glu Glu Asn Thr Ser Lys Asn Val Pro Val Gln Lys Gly Ser Pro Val
        210                 215                 220

Gln Leu Gly Ala Lys Ser Lys Gly Ala Pro Phe Lys Pro Pro Lys Glu
225                 230                 235                 240

Asp Pro Glu Asp Lys Asp His Gly Ala Pro Ser Ser Pro Phe Pro Gly
                245                 250                 255

Val Val Leu Lys Pro Ala Ala Ser Arg Gly Ser Pro Gly Leu Ser Lys
                260                 265                 270

Asn Phe Glu Glu Lys Lys Glu Asp Arg Lys Thr Asp Leu Ala Lys Asn
            275                 280                 285

Ile Phe Leu Asn Lys Leu Asn Gln Glu Glu Pro Ala Arg Phe Pro Lys
        290                 295                 300

Ala Pro Ser Lys Leu Thr Ala Gly Thr Pro Trp Gly Gln Ser Gln Glu
305                 310                 315                 320
```

-continued

```
Lys Glu Gly Asp Lys Asn Ser Ala Thr Pro Lys Gln Lys Ala Leu Pro
            325                 330                 335

Pro Leu Ser Val Leu Gly Pro Pro Pro Lys Pro Asn Arg Pro Pro
        340                 345                 350

Asn Val Asp Leu Thr Arg Phe Arg Lys Ala Asp Ser Ala Asn Ser Ala
            355                 360                 365

Thr Lys Ser Gln Thr Pro Tyr Ser Thr Thr Ser Leu Pro Pro Pro
    370                 375                 380

Pro Thr His Pro Ala Ser Gln Pro Pro Leu Pro Ala Ser His Pro Ala
385                 390                 395                 400

His Pro Pro Val Pro Ser Leu Pro Pro Arg Asn Ile Lys Pro Pro Leu
                405                 410                 415

Asp Leu Lys His Pro Ile Asn Asp Glu Asn Gln Asp Gly Val Met His
                420                 425                 430

Ser Asp Gly Thr Gly Asn Leu Glu Glu Glu Gln Glu Ser Glu Gly Glu
            435                 440                 445

Thr Tyr Glu Asp Ile Asp Ser Ser Lys Glu Arg Asp Lys Lys Arg Glu
    450                 455                 460

Lys Glu Glu Lys Lys Arg Leu Glu Leu Glu Arg Lys Glu Gln Lys Glu
465                 470                 475                 480

Arg Glu Lys Lys Glu Gln Glu Leu Lys Lys Lys Phe Lys Leu Thr Gly
                485                 490                 495

Pro Ile Gln Val Ile His His Ala Lys Ala Cys Cys Asp Val Lys Gly
            500                 505                 510

Gly Lys Asn Glu Leu Ser Phe Lys Gln Gly Glu Asp Ile Glu Ile Ile
        515                 520                 525

Arg Ile Thr Asp Asn Pro Glu Gly Lys Trp Leu Gly Arg Thr Ala Arg
    530                 535                 540

Gly Ser Tyr Gly Tyr Ile Lys Thr Thr Ala Val Glu Ile Asp Tyr Asp
545                 550                 555                 560

Ser Leu Lys Arg Lys Lys Asn Ser Leu Asn Ala Val Pro Pro Arg Leu
                565                 570                 575

Val Glu Asp Asp Gln Asp Val Tyr Asp Asp Val Ala Glu Gln Asp Ala
            580                 585                 590

Pro Asn Ser His Gly Gln Ser Gly Ser Gly Met Phe Pro Pro Pro
        595                 600                 605

Pro Thr Asp Asp Glu Ile Tyr Asp Gly Ile Glu Glu Asp Asp Asp
    610                 615                 620

Asp Gly Ser Val Pro Gln Val Asp Glu Lys Thr Asn Ala Trp Ser Trp
625                 630                 635                 640

Gly Ile Leu Lys Met Leu Lys Gly Lys Asp Asp Arg Lys Lys Ser Ile
                645                 650                 655

Arg Glu Lys Pro Lys Val Ser Glu Ser Asp Asn Asn Glu Gly Ser Ser
            660                 665                 670

Leu Pro Ser Gln His Lys Gln Leu Asp Val Gly Glu Glu Val Tyr Asp
        675                 680                 685

Asp Val Asp Ala Ser Asp Phe Pro Pro Pro Ala Glu Met Ser Gln
    690                 695                 700

Gly Met Ser Val Gly Arg Ala Lys Thr Glu Lys Asp Pro Lys Lys
705                 710                 715                 720

Leu Lys Lys Gln Glu Lys Glu Glu Lys Asp Leu Arg Lys Lys Phe Lys
                725                 730                 735

Tyr Asp Gly Glu Ile Arg Val Leu Tyr Ser Thr Lys Val Ala Ser Ser
```

```
                    740                 745                 750
Leu Thr Ser Lys Lys Trp Gly Ala Arg Asp Leu Gln Ile Lys Pro Gly
            755                 760                 765

Glu Ser Leu Glu Val Ile Gln Ser Thr Asp Thr Lys Val Leu Cys
        770                 775                 780

Arg Asn Glu Glu Gly Lys Tyr Gly Tyr Val Leu Arg Ser Tyr Leu Val
785                 790                 795                 800

Asp Asn Asp Gly Glu Ile Tyr Asp Asp Ile Ala Asp Gly Cys Ile Tyr
                805                 810                 815

Asp Asn Asp
```